US006277634B1

(12) United States Patent
McCall et al.

(10) Patent No.: US 6,277,634 B1
(45) Date of Patent: *Aug. 21, 2001

(54) OPTIMIZED MINIZYMES AND MINIRIBOZYMES AND USES THEREOF

(75) Inventors: Maxine J. McCall, Putney; Philip Hendry, Leichhardt; Trevor Lockett, Denistone, all of (AU)

(73) Assignee: Commonwealth Scientific and Industrial Research Organization, Parkville (AU)

( * ) Notice: Subject to any disclaimer, the term of this patent is extended or adjusted under 35 U.S.C. 154(b) by 0 days.

This patent is subject to a terminal disclaimer.

(21) Appl. No.: 08/973,568

(22) PCT Filed: Jun. 7, 1996

(86) PCT No.: PCT/AU96/00343

§ 371 Date: May 15, 1998

§ 102(e) Date: May 15, 1998

(87) PCT Pub. No.: WO96/40906

PCT Pub. Date: Dec. 19, 1996

Related U.S. Application Data

(63) Continuation of application No. 08/574,396, filed on Dec. 18, 1995, now Pat. No. 6,001,648, which is a continuation-in-part of application No. 08/488,181, filed on Jun. 7, 1995, now Pat. No. 6,004,806.

(51) Int. Cl.[7] ........................... C07H 21/04; C12N 15/85; C12N 1/21; C12N 15/63
(52) U.S. Cl. ........................ 435/325; 435/6; 435/91.31; 435/320.1; 435/252.3; 536/23.1; 536/23.2; 536/24.5
(58) Field of Search .................. 435/6, 91.31, 172.3, 435/325, 252.3, 320.1, 375, 377; 536/23.1, 232, 24.5; 514/44

(56) References Cited

U.S. PATENT DOCUMENTS

| 4,511,713 | 4/1985 | Miller et al. |
| 4,987,071 | 1/1991 | Cech et al. |
| 5,023,243 | 6/1991 | Tullis. |
| 5,149,796 | 9/1992 | Rossi et al. |
| 5,298,612 | * 3/1994 | Jennings et al. ............... 536/23.2 |

FOREIGN PATENT DOCUMENTS

| 9051301 | 11/1990 | (AU). |
| 9062186 | 3/1991 | (AU). |
| 321201 | 12/1988 | (EP). |
| 8804300 | 6/1988 | (WO). |
| 9103162 | 3/1989 | (WO). |
| 8905852 | 6/1989 | (WO). |

OTHER PUBLICATIONS

Agrawal, S. "Antisense Oligonucleotides: Towards Clinical Trials" TIBTECH vol. 14:376–387, Oct. 1996.*

Branch, A. "A Good Antisense Molecule is Hard to Find" TIBS vol. 23:45–50, Feb. 1998.*

Tuschl et al. "Hammerhead Ribozymes: Importance of Stem–Loop II for Activity" PNAS vol. 90:6991–6994, Aug. 1993.*

Boehm, S., (1987), "Similarities Between a Predicted Secondary Structure for the $M_1$ RNA Ribozyme and the tRNA Binding Center of 16S rRNA from *E. coli*" FEBS Letters, 220: 283–287.

Bruening, G. (1989) "Compilation of Self–Cleaving Sequences from Plant Virus Satellite RNAs and Other Sources", Methods in Enzymology 180: 546–558.

Cameron, F.H. et al., (1989) "Specific Gene Suppression by Engineered Ribozymes in Monkey Cells" Proc. Natl. Acad. Sci. U.S.A. 86: 9139–9143.

Cech, T.R., (1987) "The Chemistry of Self–Splicing RNA Enzymes", Science, 236: 1532–1539.

Chuat, J. et al. (1989) "Can Ribozymes Be Used To Regulate Procaryote Gene Expression?", Biochemical and Biophysical Research Communications 162: 1025–1029.

Cotten, M. et al. (1989) "Ribozyme Mediated Destruction of RNA in vivo" The EMBO Journal 8: 3861–3866.

Dahm, S.C. & Uhlenbeck, O.C. (1990) "Characterization of deoxy– and ribo–containing oligonucleotide substrates in the hammerhead self–cleavage reaction" Biochimie 72: 819–823.

Eckner, R. et al. (1991) "Mature mRNA 3' End Formation Stimulates RNA Export from the Nucleus" The EMBO Journal 10: 3513–3522.

Forster, A.C. et al., (1988) "Self–cleaving Viroid and Newt RNAs May Only Be Active As Dimers" Nature 334: 265–267.

Forster, A.C. et al., (1987) "Self–Cleaving of Virusoid Is Performed by the Proposed 55–Nucleotide Active Site" Cell 50: 9–16.

Goodchild J. & Kohli, V. (Oct. 21–24, 1990.) "Ribozymes That Cleave an RNA Sequence form Human Immunodeficiency Virus. Poster number 12 at Conference in San Diego, California on Catalytic RNA as an anti–HIV agent: Design and Delivery to Cells".

(List continued on next page.)

Primary Examiner—Sean McGarry
(74) Attorney, Agent, or Firm—John P. White; Cooper & Dunham LLP

(57) ABSTRACT

This invention is directed to improved catalytic compounds, minizymes and miniribozymes, capable of hybridizing with a target RNA to be cleaved. The minizymes and miniribozymes and compositions of the present invention may be used in vitro or in vivo. They may be used as diagnostic or therapeutic agents.

46 Claims, 4 Drawing Sheets

OTHER PUBLICATIONS

Goodchild, J. & Kohli, V. (Feb. 1, 1991) Arch. Biochem. Biophys. 284: 386–391. "Ribozymes That Cleave an RNA sequence from Human Immunodeficiency Virus: the Effect of Flanking Sequence on Rate.".

Hendry, P. et al., (1992) "A Ribozyme With DNA In The Hybridising Arms Displays Enhanced Cleavage Ability" Nucleic Acids Research 20: 5737–2741.

Haseloff, J. et al., (1989) "Sequence Required for Self–cataplysed Cleavage of the Satellite RNA of Tobacco Ringspot Virus" Gene 82:43–52.

Haseloff, J. and Gerlach, W.L., (1989) "Simple RNA Enzyme with New and Highly Specific Endoribonuclease Activities" Nature, 334: 585–591.

Huillier, A. et al., Ribozyme mediated suppression of α lactalbumin Expressed in C1271 Cells by T7/Vaccinia Virus (Abstract from conference proceedings) 51st Conference of the New Zealand Society of Animal Production, New Zealand, Feb. 11–15, 1991.

Hutchins, C.J. et al., (1986) "Self–Cleavage of Plus and Minus RNA Transcripts of Avocado Sunblotch Virus" Nucleic Acids Research, 14: 3627–3635.

Jeffries, A.C. & Symons, R.H. (Feb. 25, 1989) Nucl. Acids. Res. 17: 1371–1377. "A catalytic 13–mer.".

Kikuchi, U. et al., (1991) "Site–specific cleavage of natural mRNA sequences by newly designed hairpin catalytic RNAs" Nucleic Acids Research, 19: 6751–6755.

Koizumi et al., (1988) "Construction of a Series of Several, Self–Cleavage RNA Duplexes Using Synthetic 21–mers" FEBS Letters, 228:228–230.

Koizumi et al., (1989) "Design of RNA Enzymes Distinguishing a Single Base Mutation in RNA" Nucleic Acids Research 17: 7059–7071.

Lamb, J.W. & Hay, R.T. (1990) "Ribozymes that Cleave Potato Leafroll Virus RNA Within the Coat Protein and Polymerase Genes", J. Gen. Virol. 71: 2257–2264.

McCall, M.J. et al. (1992) "Minimal Sequence Requirements For Ribozyme Activity" Proc. Natl. Acad. Sci. USA 89: 5710–5714.

McClain, et al., (1987) "Model Substrates for an RNA Enzyme" Science 238: 527–530.

Miller, W.A. et al., (1991) "A Satellite RNA of Barley Yellow Dwarf Virus Contains a Novel Hammerhead Structure in the Self–Cleavage Domain" Virology, 183: 711–720.

Perreault, J–P. et al., (1991) "Mixed Deoxyribo– and Ribo–Oligonucleotides with Catalytic Activity" Nature 344: 565–567.

Perreault, J–P. et al. (1991) "Relationship Between 2'–Hydroxyls and Magnesium Binding in the Hammerhead RNA Domain: a Model for Ribozyme Catalysis." Biochem. 29: 10695–10702.

Ruffner, D.E. et al., (1989) "Studies on the Hammerhead DNA Self–Cleaving Domain" Gene 82: 31–41.

Ruffner, D.E. et al., (1990) "Sequence Requirements of the Hammerhead RNA Self–Cleaving Reaction" Biochemistry 29: 10695–10702.

Sampson et al., (1987) "Characterization of Two–RNA catalyzed RNA Cleavage Reactions" Cold Spring Harbor Sym. Quant. Biol. 52: 267–275.

Sarver, N. et al. (1990) "Ribozymes as Potential Anti–HIV–1 Therapeutic Agents" Science, 247: 1222–1224.

Saxena, S. et al., (1990) "Ribozymes Correctly Cleave a Model Substrate and Endogenous RNA in vivo" J. Biol. Chem. 265:17106–17109.

Scanlon, K. et al., (1991) "Ribozyme–Mediated Cleavage of C–fos RNA Reduces Gene Expression of DNA Synthesis Enzymes and Metallothionein" Proc. Natl. Acad. Sci. USA, 88: 10591–10595.

Sheldon, C.C. & Symons, R.H., (1989) "RNA Stem Stability in the Formation of a Self–Cleaving Hammhead Structure" Nucleic Acids Research, 17: 5665–5678.

Symons, R.H. (1989) "Self–Cleavage of RNA in the Replication of Small Pathogens of Plants and Animals" Tibs 14: 445–450.

Tabler, M. & Tsagris, M., (1991) "Catalytic Antisense RNAs Produced by Incorporating ribozymes Sassettes into cDNA" Gene 108: 175–183.

Uhlenbeck et al., (1987) "A Small Catalytic Oligonucleotide" Nature 328: 596–600.

Uhlmann et al., Chemical Reviews (1990) 90: 544–584.

Weerasinghe, M. et al., (1991) "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme" Journal of Virology 65: 5531–5534.

Yang, J., Perreault, J–P., Labuda, D., Usman, N. & Cedergren, R., (Dec. 25, 1990) Biochemistry 29: 11156–11160. "Mixed DNA/RNA Polymers are Cleaved by the Hammerhead Ribozyme.".

Zaug, A.J. & Cech, T.R., (1986 A) "The Interviewing Sequence RNA of Tetrahymena is an Enzyme" Science, 231: 473–474.

Zaug, A.J. et al., (1986 B) "The Tetrahymena Ribozyme Acts like and RNA Restriction Endonuclease" Nature, 234: 429–433.

Benseler, F., Du, D–J., Ludwig, J. and McLaughlin, L.W. (1993) *J. Am. Chem. Soc.* 115, 8483–8484. "Hammerhead–like molecules containing non–nucleoside linkers are active RNA Catalysts.".

Hendry, P., Moghaddam, M.J., McCall, M.J., Jennings, P.A., Ebel, S. and Brown, T. (1994) *Biochim et Biophys Acta* 1219, 405–412. "Using linkers to investigate the spatial separation of the conserved nucleotides A9 and G12 in the hammerhead ribozyme.".

Long, D.M. and Uhlenbeck, O.C. (1994) *Proc. Natl. Acad. Sci.* USA 91, 6977–6981. "Kinetic characterization of intromolecular and intermolecular hammerhead RNAs with stem II deletions.".

Tuschl, T. And Eckstein, F. (1993) *Proc. Natl. Acad. Sci.* USA 90, 6991–6994. "Hammerhead ribozymes: importance of stem–loop II for activity.".

Fu, D.J. and McLaughlin, L.W. (1992) *Proc. Natl. Acad. Sci.* USA 89, 3985–3989. "Importance of specific purine amino and hydroxyl groups for efficient cleavage by a hammerhead ribozyme.".

Fu, D.J. and McLaughlin, L.W. (1992) *Biochemistry* 31, 10941–10949. "Importance of specific adenosine N7–nitrogens for efficient cleavage by a hammerhead ribozyme. A model for magnesium binding.".

Fu, D.J., Rajur, S.B. and McLaughlin, L.W. (1993) *Biochemistry* 32, 10629–10637. "Importance of specific guanosine N7–nitrogens and purine amino groups for efficient cleavage by a hammerhead ribozyme.".

Grasby, J.A., Jonathan, P., Butler, G. and Gait, M.J. (1993) *Nucl. Acids Res.* 21, 4444–4450. "The synthesis of oligoribonucleotides containing O6–methylguanosine: the role of conserved guanosine residues in hammerhead ribozyme cleavage.".

Heidenreich, O. And Eckstein, F. (1992) *J. Biol. Chem.* 267, 1904–1909. "Hammerhead ribozyme–mediated cleavage of the long terminal repeat RNA of human immunodeficiency virus type I.".

Heldenreich, O., Benseler, F., Fahrenholz and Eckstein, F. (1994) *J. Biol. Chem.* 269, 2131–2138. "High activity and stability of hammerhead ribozymes containing 2'–modified pyrimidine nucleosides and phosphorothioates.".

Hendrix, C., Mahieu, M., Anne, J., Van Calenbergh, S., Van Aerschot, A., Content, J. and Herdewijn, P. (1995) *Biochem. Biophys. Res. Comm.* 210, 67–73. "Catalytic activity and stability of hammerhead ribozymes containing 2'–acetamido–2'–deoxyribonucleosides.".

Paolella, G., Sproat, B.S. and Lamond, A.I. (1992) *EMBO J.* 11, 1913–1919. "Nuclease resistant ribozymes with high catalytic activity.".

Shimayama, T., Nishikawa, F., Nishikawa, S. and Taira, K. (1993) *Nucl. Acids Res.* 21, 2605–2611. "Nuclease–resistant chimeric ribozymes containing deoxyribonucleotides and phosphorothioate linkages.".

Slim, G. and Gait, M.J. (1992) *Biochem. Biophys. Res. Comm.* 183, 605–609. "The role of the exocyclic amino groups of conserved purines in hammerhead ribozyme cleavage.".

Taylor, N.R., Kaplan, B.E., Swiderski, P., Li, H. and Rossi, J.J. (1992) *Nucl. Acids Res.* 20, 4559–4565. "Chimeric DNA–RNA hammerhead ribozymes have enhanced in vitro catalytic efficiency and increased stability in vivo.".

Tuschl. T., Ng. M.M., Pieken, W., Benseler, F. And Eckstein, F. (1993) *Biochemistry* 32, 11658–11668, "Importance of exocyclic base funstional groups of central core guanosines for hammerhead ribozyme activity.".

Uesugi, S., Kodama, H., Hiroaki, H. and Odai, O. (1992) *Nucl. Acids Symp. Ser.* 27, "Properties of hammerhead–type RNA enzyme derivatives which contain a G–to–I replacement in the loop region.".

Williams, D.M., Pieken, W.A. and Eckstein F. (1992) *Proc. Natl. Acad. Sci. USA* 89, 918–921. "Function of specific 2'hydroxyl groups of guanosines in a hammerhead ribozyme probed by 2' modifications.".

Yang, J.H., Usman, N., Chartrand, P. And Cedergren, R. (1992) *Biochemistry* 31, 5005–5009. "Minimum ribonucleotide requirement for catalysis by the RNA hammerhead domain.".

* cited by examiner

OPTIMIZED MINIZYMES AND MINIRIBOZYMES AND USES THEREOF

This application is a national stage application of PCT International Application No. PCT/AU96/00343, filed Jun. 7, 1996, which is a continuation of U.S. Ser. No. 08/574,396, filed Dec. 18, 1995 and now U.S. Pat. No. 6,001,648, which is a continuation-in-part of U.S. Ser. No. 08/488,181, filed Jun. 7, 1995 and now U.S. Pat. No. 6,004,806.

Throughout this application various references are cited in bracket by author and publication year. The full citations are listed alphabetically and may be found immediately preceding the claims. These publications are hereby incorporated by reference into the present application.

BACKGROUND OF THE INVENTION

Several types of ribozymes have been identified in living organisms. One of the first ribozymes to show catalytic turnover was the RNA moiety of ribonuclease P. Ribonuclease P (RNase P) cleaves precursor tRNAs (pre-tRNAs) at their 5' ends to give the mature 5'-termini of tRNAs. In *Escherichia coli* and *Bacillus subtilis*, the RNase P holoenzyme is composed of one basic protein subunit of approximate $M_r$ 14,000 (119 amino acids) and one single stranded RNA molecule of 377 and 401 nucleotides, respectively [Baer, 1990; Altman 1987; Waugh, 1989; Pace, 1990; Nichols, 1988]. Another early ribozyme to show cleavage was the L-19 intervening sequence (IVS) from tetrahymena. The 413 nucleotide intervening sequence (IVS) in the nuclear rRNA precursor from *Tetrahymena thermophila* can be excised and the two exons ligated in the complete absence of any protein [Kruger, 1982; Cech, 1981]. Unique to this class of self-splicing reaction is the requirement of a guanosine or 5' guanosine nucleotide cofactor. The hammerhead, which in nature undergoes a self-cleavage reaction, constitutes a third class of ribozymes. A number of plant pathogenic RNAs [Symons, 1989; Symons, 1990; Bruening, 1989; Bruening 1990], one animal viral RNA [Taylor, 1990] and a transcript from satellite II of DNA of the newt [Epstein, 1987; Epstein 1989] and from a Neurosoora DNA plasmid [Saville, 1990] undergo a site specific self-cleavage reaction in vitro to produce cleavage fragments with a 2',3'-cyclic phosphate and a 5'-hydroxyl group. This reaction is unlike RNase P RNA cleavage of pre-tRNAs, where the internucleotide bond undergoes a phosphoryl transfer reaction in the presence of $Mg^{++}$ or other divalent cations. Metal cations may be essential to RNA catalysis [Pyle, 1993]. Other reactions documented to date show that ribozymes can catalyze the cleavage of DNA [Robertson, 1990; Herschlag 1990], the replication of RNA strands [Green, 1992], the opening of 2'-3'-cyclic phosphate rings [Pan, 1992], as well as react with phosphate monoesters [Zaug, 1986] and carbon centers [Noller, 1992; Piccirilli, 1992]. Finally, ribozymes with new kinds of catalytic reactivity are being created through techniques of in vitro selection and evolution [Breaker and Joyce, 1994; Szostak, 1992].

The ability to design a ribozyme to specifically target and cleave any designated RNA sequence ha, led to much interest in the potential application of hammerhead ribozymes in transgenic plants and in animal health as gene therapy agents or drugs. To improve the ability to treat a disease or target a specific nucleic acid, it is desirable to optimize the ribozyme to achieve the maximum cleavage activity. While much success has been achieved in vitro in targeting and cleaving a number of designated RNA sequences (Saxena and Ackerman, 1990; Lamb and Hay, 1990; Evans, et al., 1992; Mazzolini, et al., 1992; Homann, et al., 1993), there are fewer whole cell examples.

Previous reports have demonstrated that high levels of ribozyme expression are required to achieve reduced accumulation of target sequence in vivo [Cameron and Jennings, 1989; Cotten and Birnsteil, 1989; Sioud and Drilca, 1991; L'Huillier, et al., 1992; Perriman et al., 1993]. Another article suggests a necessity for the target and ribozyme to be sequestered in the same cellular compartment [Sullenger and Cech, 1993]. These reports demonstrate that hammerhead ribozymes are clearly capable of specific cleavage of a designated target RNA within a biological system.

SUMMARY OF THE INVENTION

This invention is directed to improved catalytic compounds, minizymes and miniribozymes, capable of hybridizing with a target RNA to be cleaved. The minizymes and miniribozymes and compositions of the present invention may be used in vitro or in vivo. They may be used as diagnostic or therapeutic agents.

Figure 1:
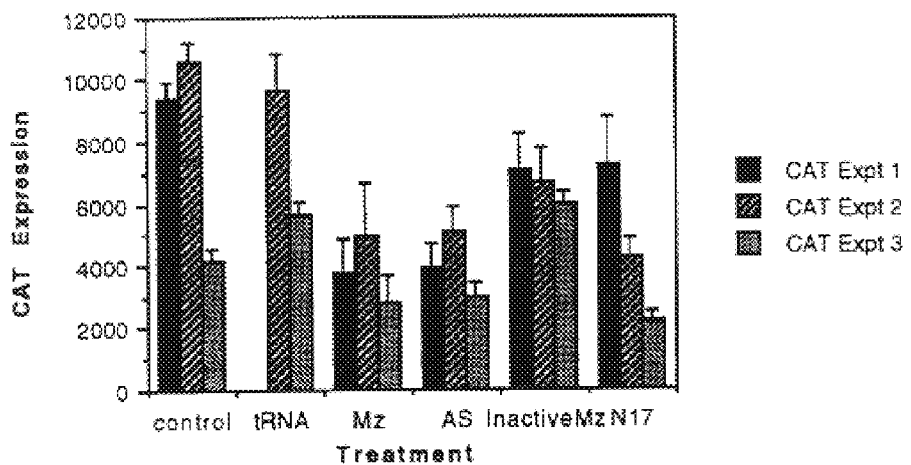
FIG. 1 shows the CAT Expression (Mean±SEM (Standard Error of the Mean)) for Different treatments. Each experiment is performed in triplicate.

Sequence of miniribozyme IL2MGUUUUC is 5' CAAUGCAA CUGAUGA GUUUUC GAAAC AGGa 3' (SEQ. ID NO. 49) and ribozyme IL2RA is 5' CAAUGCAA CUGAUGA GUCCUUUUGGAC GAAAC AGGa 3' (SEQ. ID NO. 50).

The target sequence within the II,2 transcript is 5' UCCUGUC*UUGCAUUG 3' (SEQ. ID NO. 51), where * represents the cleavage site which is 82 nucleotides from the 5' end. Conditions for cleavage experiment: 50 mM Tris.HCl, pH 8, 10 TrLM $MgCl_2$, 0.2 µM transcript, 1 µM miniribozyme or ribozyme, transcript internally labelled, no heat-denaturing or heat-annealing step was performed.

DETAILED DESCRIPTION OF THE INVENTION

This invention is directed to a compound having the formula (Seq ID No. 3):

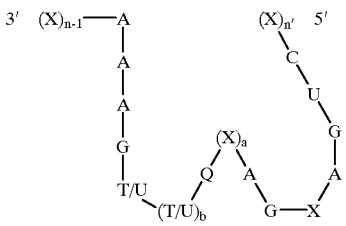

wherein each X represents a nucleotide which may be the same or different and Q represents guanidine and may be substituted or modified in its sugar, base or phosphate; wherein each of $(X)_n$ and $(X)_{n'}$ represents an oligonucleotide having a predetermined sequence which is capable of hybridizing with an RNA target sequence to be cleaved; wherein each of n and n' represents an integer which defines the number of nucleotides in the oligonucleotide; wherein each solid line represents a chemical linkage providing covalent bonds between the nucleotides located on either side thereof; wherein "a" represents an integer which defines a number of nucleotides with the proviso that "a" may be 0 or 1 and if 0, the A located 5' of (YX) a is bonded to the G located 3' of $(X)_a$; and wherein $(T/U)_b$ represents an oligonucleotide with the proviso that "b" represents an integer which is 3 or 4.

Alternatively, the compound may have the formula (Seq ID No. 4):

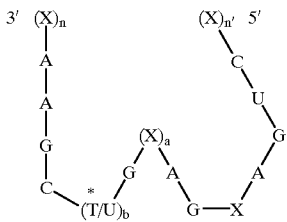

In the compounds above, the oligonucleotide 3'-$(X)_n$— is 3'-$(X)_{n-1}$—A— or is 3'-$(X)_{n-2}$—C—A—. Preferably, $(X)_a$ is absent.

The integer "b" of (T/U) b is preferably equal to 3 or 4. Preferably, $(T/U)_b$ is a $(T)_b$.

The invention is also directed to compositions comprising the compounds above in association with an acceptable carrier; the carrier is preferably a pharmaceutically acceptable carrier.

The invention is also directed to an oligonucleotide transfer vector containing a nucleotide sequence which on transcription gives rise to the compound above. The transfer vector may be a bacterial plasmid, a bacteriophage DNA, a cosmid, an eukaryotic viral DNA, a plant DNA virus, a composite geminivirus, a binary plant expression vector (Ri or Ti) an infective phage particle or a portion thereof. The packaged oligonucleotide transfer vector may contain promoter sequences for RNA polymerase II, human tRNA$^{val}$, plant tRNA, human tRNA, snRNA promoter or RNA polymerase III. The invention also includes a host cell transformed by the transfer vector. The host cell is a prokaryotic host cell, an eukaryotic host cell, an E. coli host cell, a monkey COS host cell, a Chinese hamster ovary host cell, a mammalian host cell, a plant host cell, a plant protoplast host cell, a hematopoietic host cell, a stem cell, a hematopoietic progenitor cell, a lymphoid cell, T-cell, a B-cell, pre-B cell, a CD4+T-cell or a peripheral blood mononuclear cell.

The invention also provides a method of cleaving a target mRNA in a subject which comprises administering to the subject an effective amount of the compound above or a vector capable of expressing the compound. The administration may be topical in an amount between 1 ng and 10 mg. The administration may also be systemic and administered in an amount between 1 ng and 500 μg/kg weight/day. The administration may also be aerosol administration. The invention also provides a method of cleaving a target mRNA in a host cell which comprises administering to the host cell an effective amount of the compound above.

The compound above may further comprise an antisense nucleic acid which is capable of hybridizing with an RNA target sequence. The compound above may further comprise at least one additional non-naturally occurring oligonucleotide compound which comprises nucleotides whose sequence defines a conserved catalytic region and nucleotides whose sequence is capable of hybridizing with a predetermined target sequence. The additional non-naturally occurring oligonucleotide compound may be a hammerhead ribozyme, a minizyme, a hairpin ribozyme, a hepatitis delta ribozyme, an RNAase P ribozyme or a combination thereof. See for example hammerhead ribozyme Haseloff et al.. U.S. Pat. No. 5,254,678, issued Oct. 18, 1993; Jennings U.S. Pat. No. 5,298,612, issued Mar. 29, 1994; Group I introns, Cech et al. U.S. Pat. No. 4,740,463, issued Apr. 26, 1988; Altman et al. U.S. Pat. No. 5,168,053, issued Dec. 1, 1992 or PCT International Publication No WO 92/03566), hepatitis delta ribozymes (e.g. Blumenfeld et al. PCT International Application No. WO/90/05157) and hairpin ribozymes (European Patent Application No. EP 360,257, Hampel et al. Nuc. Acids Res. (1990) 18:299–304).

Preferred cleavage sites in the target RNA have the sequence "XUX", preferably GUC, GUU, GUA, UUA and UUC. By way of example, suitable reaction conditions may comprise a temperature from about 4 degree(s) C. to about 60 degree(s) C., preferably from about 10 degree(s) to 45 degree(s) C., more preferably from about 20 degree(s) to 43 degree(s) C., pH from about 6.0 to about 9.0 and concentration of divalent cation (such as $Mg^{2+}$) from about 1 to about 100 mM (preferably 1 to 20 mM). The nucleotides of the sequences $(X)_n$ and $(X)_{n'}$ of the compounds above may be of any number and sequence sufficient to enable hybridization with the nucleotides in the target RNA, as described herein. Ribozymes containing a small number of nucleotides in each of the groups $(X)_n$ and $(X)_{n'}$ of the compounds above (such as four nucleotides) would generally be incubated at lower temperatures, such as about 20 degree(s) C. to about 25 degree(s) C. to aid hybridizing with the nucleotide sequences in the substrate. The number of nucleotides n and n' in $(X)_n$ and $(X)_{n'}$ are not necessarily equal. The invention is also directed to covalently-linked multiple ribozymes, where each ribozyme is directed to a target sequence which may be the same or different. In addition these compounds may be covalently attached to an antisense molecule which may be 10 to 100 bases in length. Antisense sequences capable of hybridizing to an RNA in a mammal or plant are well known see (Shewmaker et al. U.S. Pat. No. 5,107,065, issued Apr. 21, 1992). As the ribozyme acts as an enzyme, showing turnover, the ratio of ribozyme to substrate may vary widely.

A target RNA containing a suitable cleavage site such as XUX site may be incubated with a compound described above. The nucleotide sequences $(X)_n$ and $(X)_{n'}$ of the compounds above are selected to hybridize with their substrate. They may be selected so as to be complementary to nucleotide sequences flanking the cleavage site in the target RNA. On incubation of the ribozyme or ribozyme composition and its substrate, an enzyme/substrate complex is formed as a result of base pairing between corresponding nucleotides in the ribozyme and the substrate. Nucleotide sequences complementary to $(X)_n$ and $(X)_{n'}$ of the compounds above flanking the cleavage site in the substrate may form a double stranded duplex with $(X)_n$ and $(X)_{n'}$ as a result of base pairing, which base pairing is well known in the art [See for example: Sambrook, 1989]. The formation of a double stranded duplex between the nucleotides may be referred to as hybridization [Sambrook, 1989]. The extent of hybridization or duplex formation between the ribozyme and its substrate can be readily assessed, for example, by labeling one or both components, such as with a radiolabel, and then subjecting the reaction mixture to polyacrylamide gel electrophoresis under non-denaturing conditions [Sambrook, 1989]. If the target is cleaved specifically on incubation with the compound, the compound is active and falls within the scope of this invention. Accordingly, a ribozyme containing substituted or modified nucleotides in the conserved region may be simply tested for endonuclease activity in a routine manner.

As will be readily appreciated by workers in the field to which this invention relates, the cleavage of a target RNA may be readily assessed by various methods well known in the art [See for example: Sambrook, 1989]. Cleavage may, for example, be assessed by running the reaction products (where the substrate is radioactively labeled) on acrylamide, agarose, or other gel systems under denaturing conditions, and then subjecting the gel to autoradiography or other analytical technique to detect cleavage fragments [Sambrook, 1989].

In another embodiment, the invention provides a composition which comprises the compounds above in association with an acceptable carrier.

The invention is also directed to an oligonucleotide transfer vector containing a nucleotide sequence or sequences which on transcription gives rise to the compounds above. The transfer vector may be a bacterial plasmid, a recombinant bacterial plasmid, a bacteriophage DNA, a cosmid, or an eukaryotic viral DNA. The transfer vector may also contain an appropriate transcription promoter sequence such as that for RNA polymerase II, RNA polymerase III, a viral promoter such as SV40 or HIV LTR, a plant promoter such as CaMV S35 or a promoter associated with animal health. The vector may also contain an appropriate termination sequence. Preferably, the plant or animal promoter is capable of expression in a regulated manner. Such promoter control regions would be regulated by endogenous signals to direct either tissue specific or temporal expression or by externally administered compounds to elicit transcription of downstream sequences. It may also contain sequences to effect integration into the host genome on episomal replication in the host cell.

The invention also provides a host cell transformed by the transfer vector as mentioned above, which may be a prokaryotic host cell or an eukaryotic host cell e.g. yeast cell or yeast protoplast, *E. coli* host cell, a monkey host cell (e.g. COS), a Chinese hamster ovary host cell, a mammalian host cell, a plant host cell, or a plant protoplast host cell.

In one embodiment, there is provided a packaged oligonucleotide transfer vector, as mentioned hereinabove, which is a plant virus, a composite mammalian virus, a geminivirus, a Ti or Ri plasmid, an infective phage particle or portion thereof.

In another embodiment, the composition, as discussed above, is in association with an acceptable carrier. This invention also provides a composition as discussed hereinabove wherein the oligonucleotide is an oligoribonucleotide or an RNA-DNA hybrid molecule comprising nucleotides which may be substituted or modified in their sugar, base or phosphate group. It is preferred that the oligonucleotide be an oligoribonucleotide or a hybrid RNA-DNA molecule. However, other substitutions or modifications in the nucleotide are possible providing that endonuclease activity is not lost. Such derivatives or modifications are described below.

The nucleotides may be in the form of dieoxyribonucleotides, ribonucleotides, deoxyribonucleotide ribonucleotide hybrids, or derivatives thereof as herein described. The flanking sequences $(X)_n$ and $(X)_{n'}$ may be chosen to optimize stability of the ribozyme from degradation. For example, deoxyribonucleotides are resistant to the action of ribonucleases. Modified bases, sugars or phosphate linkages of rucleotides, such as phosphoramidate, or phosphorothioate linkages in the sugar phosphate chain of $X_n$ and $X_{n'}$, may also provide resistance to nuclease attack. Binding affinity may also be optimized in particular circumstances, by providing nucleotides solely in the form of ribonucleotides, deoxyribonucleotides, or combinations thereof. In some circumstances it may be necessary to optimize the composition of the sequences $(X)_n$ and $(X)_{n'}$, to maximize target RNA cleavage. The cleavage activity of ribozymes having flanking nucleotide sequences which hybridize to target sequences and which are comprised wholly of deoxyribonucleotides may, in some circumstances, have reduced activity. In such circumstances optimization may involve providing a mixture of deoxyribonucleotides and ribonucleotides in the nucleotide sequences $(X)_n$ and $(X)_{n'}$. For example, nucleotides in the ribozyne which are proximal to the cleavage site in a target RNA may be in the form of ribonucleotides.

The respective 3' and 5' termini of the sequences $(X)_n$ and $(X)_{n'}$ or alternatively the 3' and 5' end termini of the ribozyme, may be modified to stabilize the ribozyme from degradation. For example, blocking groups may be added to prevent terminal nuclease attack, in particular 3'–5' progressive exonuclease activity. By way of example, blocking groups may be selected from substituted or unsubstituted alkyl, substituted or unsubstituted phenyl, substituted or unsubstituted alkanoyl. Substituents may be selected from $C_1$–$C_5$ alkyl; halogens such as F, Cl or Er; hydroxy; amino; $C_1$–$C_5$ alkoxy and the like. Alternatively, nucleotide analogues such as phosphorothioates, methylphosphonates or phosphoramidates or nucleoside derivatives (such as alpha—anomer of the ribose moiety) which are resistant to nuclease attack may be employed as terminal blocking groups. The blocking group may be an inverted linkage such as a 3' 3' thymidine linkage or a 5' 5' pyrophosphate linkage as in the guanosine cap.

Alternatively, groups which alter the susceptibility of the ribozyme molecule to other nucleases may be inserted into the 3' and/or 5' end of the ribozyme. For example, 9-aminoacridine attached to the ribozyme may act as a terminal blocking group to generate resistance to nuclease attack on the ribozyme molecules and/or as an intercalating agent to aid endonucleolytic activity. It will be readily appreciated that a variety of other chemical groups, e.g. spermine or spermidine could be used in a related manner.

It is also possible to stabilize the ribozyme from degradation by embedding it in an RNA molecule. These molecules can be produced either in vitro or in vivo by DNA coding sequences being operably linked to transcriptional control sequences as appropriate. Examples of RNA molecules into which ribozymes could be inserted may include, but are not limited to, tRNA, mRNA, rRNA, snRNA or other RNA molecules. In addition, the ribozyme may be inserted into an engineered stable stem loop structure. The compound may also be coupled with other stabilizing structures such as a transcription terminator on the 3' end such as the T7 terminator, ρ-independent terminator, cry element (Gelfand et al. U.S. Pat. No. 4,666,848, issued May 19, 1987) or the TrpE terminator. Furthermore, sequences such as the poly (A) addition signal AATAAA may be added. In addition, strategies involving changing the length of the 3' non-coding region may be used (see Gillies, U.S. Pat. No. 5,149,635, issued Sep. 22, 1992). Alternatively, a stabilizing sequence or protein binding domain such as Sioud, PCT International application WO 94/10301 may be used. Further, it is possible to insert the compound into a DNA molecule as well.

The compounds of this invention may be covalently or non-covalently associated with affinity agents such as proteins, steroids, hormones, lipids, nucleic acid sequences, intercalating molecules (such as acridine derivatives, for example 9-amino acridine) or the like to modify binding affinity for a substrate nucleotide sequence or increase affinity for target cells, or localization in cellular compartments or the like. For example, the ribozymes of the present invention may be associated with RNA binding peptides or proteins which may assist in bringing the ribozyme into juxtaposition with a target nucleic acid such that hybridization and cleavage of the target sequence may take place. Nucleotide sequences may be added to the respective 3' and 5' termini of the sequences $(X)_n$ and $(X)_{n'}$ or alternatively the 3' and 5' end termini of the ribozyme to increase affinity for substrates. Such additional nucleotide sequences may form triple helices with target sequences [Strobel, 1991] which may enable interaction with an intramolecularly folded substrate. Alternatively, modified bases (non-natural or modified bases as described in Principles of Nucleic Acid Structure [Saenger, 1984]) within the additional nucleotide sequences may be used that will associate with either single stranded or duplex DNA generating base pair, triplet, or quadruplet, interactions with nucleotides in the substrate. Suitable bases would include inosine, 5-methylcytosine, 5-bromouracil and other such bases as are well known in the art, as described, for example, in Principles of Nucleic Acid Structure [Saenger, 1984].

The compounds of this invention may be produced by nucleotide synthetic techniques which are known in the art, and described for example by Carruthers et al., Foehler et al. and Sproat et al. [Carruthers, 1987; Foehler, 1986; Sproat, 1984]. Generally, such synthetic procedures involve the sequential coupling of activated and protected nucleotide bases to give a protected nucleotide chain, whereafter protecting groups may be removed by suitable treatment. Preferably the compounds will be synthesized on an automated synthesizer such as those made by Applied Biosystems (a Division of Perkin Elmer), Pharmacia or Millipore. Alternatively, the ribozymes in accordance with this invention may be produced by transcription of nucleotide sequences encoding said ribozymes in host-cells or in cell free systems utilizing enzymes such as T3, SP6 or T7 RNA-polymerase.

In addition to being synthesized chemically, ribozymes with modified nucleotides may be synthesized enzymatically. The phosphodiester bonds of RNA can be replaced by phosphorothioate linkages by in vitro transcription using nucleoside a-phosphorthiotriphosphates. T7 RNA polymerase specifically incorporates the Sp isomer of α-phosphorthiotriphosphate with inversion of configuration to produce the Rp isomer of the phosphorothioate linkage. The methods to produce transcripts fully substituted with phosphorothioate linkages adjacent to a given nucleotide, or to produce partially substituted transcripts containing approximately one phosphorothioate linkage. The methods to produce transcripts fully substituted with phosphorothioate linkages adjacent to a given nucleotide, or to produce partially substituted transcripts containing approximately one phosphorothioate linkage per molecule, are described by Ruffner and Uhlenbeck (1990). Conrad et al. (1995) describe methods of using T7 RNA polymerase to produce chimeric transcripts containing ribonucleotides and deoxyribonucleotides (with and without phosphorothioate linkages), and also ribonucleotides and 2'-O-methylnucleotides (with and without phosphorothioate linkages). These methods have been shown to produce transcripts containing up to 50% deoxyribonucleotides, and up to 58% 2'-O-methylnucleotides. Aurup et al (1992) describe methods for using T7 polymerase to produce transcripts containing 2'-fluoro-2'-deoxyuridine, 2'-fluoro-2'-deoxycytidine, and 2'-amino-2'deoxyuridine. (Aurup, 1992; Conrad, 1995; Ruffner, 1990) Further means for producing the ribozymes of this invention are further discussed below [Sambrook, 1989].

Nucleotides represented in the compounds above comprise a sugar, base, and a monophosphate group or a phosphodiester linkage. Accordingly, nucleotide derivatives or modifications may be made at the level of the sugar, base, monophosphate groupings or phosphodiester linkages. It is preferred that the nucleotides in the compounds above be ribonucleotides or RNA/DNA hybrids, however, other substitutions or modifications in the nucleotide are possible providing that endonuclease activity is not lost.

In one aspect of this invention, the sugar of the nucleotide may be a ribose or a deoxyribose such that the nucleotide is either a ribonucleotide or a deoxyribonucleotide, respectively. Furthermore, the sugar moiety of the nucleotide may be modified according to well known methods in the art [See for example: Saenger, 1984; Sober, 1970]. This invention embraces various modifications to the sugar moiety of nucleotides as long as such modifications do not abolish cleavage activity of the ribozyme. Examples of modified sugars include replacement of secondary hydroxyl groups with halogen, amino or azido groups; 2'-alkylation; conformational variants such as the O2'-hydroxyl being cis-oriented to the glycosyl $C_1'$ —N link to provide arabinonucleosides, and conformational isomers at carbon $C_1'$ to give alpha -nucleosides, and the like. In addition, the invention is directed to compounds with a substituted 2' hydroxyl such as 2' O-allyl, or 2' O-methyl. Alternatively, the carbon backbone of the sugar may be substituted such as in 2' C-allyl.

Accordingly, the base of the nucleotide may be adenine, 2-amino adenine, cytosine, guanine, hypoxanthine, inosine, methyl cytosine, thymine, xanthine, uracil, or other methylated bases.

Nucleotide bases, deoxynucleotide bases, and ribonucleotide bases are well known in the art and are described, for example in Principles of Nucleic Acid Structure [Saenger, 1984]. Furthermore, nucleotide, ribonucleotide, and deoxyribonucleotide derivatives, substitutions and/or modifications are well known in the art [See for example: Saenger, 1984; Sober, 1970], and these may be incorporated in the ribozyme made with the proviso that endonuclease activity of the ribozyme is not lost. As mentioned previously, endoribonuclease activity may be readily and routinely assessed.

In addition, a large number of modified bases are found in nature, and a wide range of modified bases have been synthetically produced [See for example: Saenger, 1984; Sober, 1970]. For example, amino groups and ring nitrogens may be alkylated, such as alkylation of ring nitrogen atoms or carbon atoms such as $N_1$ and $N_7$ of guanine and $C_5$ of cytosine; substitution of keto by thick to groups; saturation of carbon-carbon double bonds, and introduction of a C-glycosyl link in pseudouridine. Examples of thioketo derivatives are 6-mercaptopurine and 6-mercaptoguanine. Bases may be substituted with various groups, such as halogen, hydroxy, amine, alkyl, azido, nitro, phenyl and the like. The phosphate moiety of nucleotides or the phosphodiester linkages of oligonucleotides are also subject to derivatization or modifications, which are well known in the art. For example, replacement of oxygen with nitrogen, sulphur or carbon gives phosphoramidates, (phosphorothioates, phosphorodithioates) and phosphonates, respectively. Substitutions of oxygen with nitrogen, sulphur or carbon derivatives may be made in bridging or non bridging positions. It has been well established from work involving antisense oligonucleotides [Uhlman, 1990] that phosphodiester and phosphorothioate derivatives may efficiently enter cells (particularly when of short length), possibly due to association with a cellular receptor. Methylphosphonates are probably readily taken up by cells by virtue of their electrical neutrality.

A further aspect of the invention provides alternative linkages such as an amide, a sulfonamide, a hydroxylamine, a formacetal, a 3'-thioformacetal, a sulfide, or an ethylene glycol function to replace the conventional phosphodiester linkage. These modifications may increase resistance towards cellular nucleases and/or improved pharmacokinetics.

Information on Synthesis of Protected Nucleotides and their Incorporation into Modified Ribozymes.

Possible Nucleotide
Modifications

Sugar Modifications may be 2' fluoro, 2' amino, 2' O-allyl, 2' C-allyl, 2' O-methyl, 2' O-alkyl, 4'-thio-ribose, α-anomer, arabinose, other sugars, or non-circular analogues.

Phosphate Modifications may be phosphorothioate (non-bridging), phosphorodithioate (non bridging), 3' bridging phosphorothioate, 5' briding phosphorothioate, phosphoramidates, 3' bridging phosphoramidate, 5' bridging phosphoramidate, methyl phosphonate, other alkyl phosphonates or phosphate triesters.

The phosphodiester linkage may be replaced by an amide, carbamate, thiocarbamate, urea, amine, hydroxylamine, formacetal, thioformacetal, allyl ether, allyl, ether, thioether, or PNA (peptide nucleic acid) linkage.

Modifications in base may be purine, 2,6-diaminopurine, 2-aminopurine, $O^6$-methylguanosine, 5-alkenylpyrimidines, 5-propyne, inosine, 5-methylcytosine, pseudouridine, abasic (ribose or deoxyribose).

Some nucleotides may be replaced with the following chemical linkers: 1,3-propane-diol, alkane-diols, or various polymers of (ethyleneglycol, tetraethylene glycol, hexaethyleneglycol).

Other Modifications to the 3' end may be selected from: 3'-3' inverted linkage (inverted diester or inverted phosphoramidate). 3'-3' linked abasic ribose, or end-capped (methoxyethylamine phosphoramidate).

Modified sugars may be synthesized as follows: 2'-deoxy-2'-fluoro uridine (Sinha, 1984); 2'-deoxy-2' fluoro cytidine (Sinha, 1984); 2'-deoxy-2' fluoroadenosine; synthesis and incorporation into ribozyme (Olsen, 1991); 2'-deoxy-2'-amino uridine and 2'-deoxy-2'-amino cytidine (Heidenreich, 1994); 2'-O-allyl-(uridine or cytidine or adenosine or guanosine) (Available from Boehringer Mannheim, Mannheim, Germany) or (Badger, 1994). 2'-deoxy-2'-C-allyl-ribonucleotides; 2'-O-methyl ribonucleotides see Review: (Sproat, B. S., 1991A) (also Available from Chemgenes, Waltham, Mass. or Glen Research, Sterling, Va. other 2'-O-alkyl-ribonucleotides, Synthesis see (Monia, B. P., 1993; Sproat, B. S., 1991B); α-anomer of uridine, cytidine, adenosine and guanosine, see (Debart, F., 1992 and references therein); Other modified sugars, etc. Arabinose (Garbesi, A., 1993); Hexose-thymidine (Augustyns, K., 1992) and linear analogues of sugars (Hendry, 1994).

Modified phosphates may be synthesized as follows: Phosphorothioate; synthesized by modification of oxidation procedure during phosphoramidite synthesis. Reagents commercially available from Perkin Elmer and others, products are mixture of isomers, some methods available for stereospecific synthesis of phosphorothioate, see ref: (Stec, 1991); Phosphorodithioate; (Eldrup, A. B., 1994; Caruthers, 1991; Beaton, 1991); 3'-bridging phosphorothioate; 5' bridging phosphorothioate; phosphoramidates (non-bridging, oxidize the phosphite triester with solution containing the required amine); (Froehler, B., 1988; Jager, A., 1988; Letsinger, R. L., 1988); 3' bridging phosphoramidate (NH replaces 3' O) (Forms very stable duplexes) (Letsinger, 1992; Gryaznov, S. M., 1995; Chen, J. K., 1995); 5' Bridging Phosphoramidate (NH replaces 5' O; thymidine analogue only, weak binder) (Gryaznov, S. M., 1992); Methylphosphonate (reagents are commercially available; Glen Research or Chemgenes Stereospecific; Rp isomers bind stronger: (Savchenko, 1994; Miller, 1991); 5'-deoxy, 5'-methylphosphonate (Szabo, 1995); Other alkylphosphonates (Fathi, 1994A; Fathi, 1994B); Phosphate triesters(Summers, 1986).

Replacements for the Phosphodiester Linkage may be synthesized as follows: For review see (De Mesmaker, 1995) Amides (Chur,1993; Blommers, 1994; De Mesmaeker, 1993; De Mesmaeker, 1994A; De Mesmaeker, 1994B; Lebreton, 1993; Lebreton, 1994A; Lebreton, 1994B; Idsiak, 1993): Carbamate (Waldner, 1994; Stirchak, 1987; Habus, 1994; Thiocarbamate (Waldner,1995); Ureas (Waldner, 1994) Amines (De Mesmaeker,1994C; Caulfield, 1994); Hydroxylamine (Debart,1992; Vasseur,1992; Formacetal (Matteucci,1990; Jones, 1993) Thioformacetal (Jones,1993); Allyl ether (Cao,1994); Allyl, Ether, Thioether (Cao, 1994); Alkane (De Mesmaeker,1994; PNA A selection of binding and antisense properties (Nielsen, 1993A; Hanvey, 1992; Egholm, 1993; Nielsen, 1993B) ; PNA Synthesis (Egholm, 1992A; Egholm, 1992B) ;Prepn of purine PNA monomers and oligos (available commercially from Millipore corporation).

Modified bases may be synthesized as follows: Purine; synthesis and incorporation into ribozyme (Slim, 1992; Fu,1992; Fu, 1993); 7-deazaGuanosine, synthesis and incorporation into ribozyme (Fu, 1993); Inosine, synthesis and incorporation into ribozyme (Slim,1992; Fu, 1993) 7-deazaAdenosine, synthesis and incorporation into ribozyme (Fu, 1992; Seela, 1993). O6-methylguanosine, synthesis and incorporation into ribozyme (Grasby, 1993); 2,6-diaminopurine, synthesis (Sproat, 1991); 2-aminopurine, synthesis and incorporation into ribozyme (Ng, 1994; Tuschl, 1993); Isoguanosine, synthesis and incorporation into ribozyme (Ng, 1994; Tuschl, 1993); Xanthosine, synthesis and incorporation into ribozyme (Tuschl, 1993); 6-azathymidine, 6-aza-2'-deoxycytidine, synthesis and incorporation into oligonucleotides (Sanghvi, 1993); 5-alkenylpyrimidines; 5-propyne (Gilead, Froehler); inosine; 5-methylcytosine; pseudouridine; abasic ribose or deoxyribose.

Summary of Nucletotide-modifications Which Have Been Tested in Ribozymes

Sugars

Modifications may be made to the 2'OH group of the sugar at all non-conserved nucleotides; modifications tested have been 2'H (DNA), 2'F, 2'amino, 2'-O-allyl, 2'-O-methyl, 2'-C-allyl. Selected modifications may be made to the 2'OH groups of the conserved nucleotides C3, U4, A6, N7, A9, G12, A13, A14, N15.2. Modifications cannot be made to the 2'OH groups of GS, G8 and A15.1.

For a ribozyme with good cleavage activity, modifications should not be made to G5, A6, G8, G12, A15.1 (except G12 can be 2'H (DNA)). Generally, except for modifications at G5, G8 and A15.1, no single modification causes a big reduction in cleavage activity; however, activity decreases as more modifications are included in the ribozyme.

Phosphates

The phosphate groups of the nonconserved nucleotides may be phosphorothioates (phosphorothioated DNA). Preferably, when non-conserved nucleotides are DNA, only two or three phosphates at the 3' and 5' ends of the ribozyme are phosphorothioates. The phosphates 5' to the conserved nucleotides C3, U4, G5, G8 and G12, and 3' to A9 and N15.2, may be phosphorothioates; but phosphates 5' to A9, A13 and A14 may not be phosphorothioates.

Conserved Nucleotides

C3

Sugar—2'-OH group can be modified (except, probably, for 2'amino). 2'H (Yang, 92), 2'F (Pieken, 91; Heidenreich, 92), 2'-O-allyl (Paolella, 92), 2'-O-Methyl (Usman, 95) are all modifications that permit cleavage. Possibly cannot have 2'amino modification (several Cs in ribozyme had 2'amino modification which resulted in reduction in activity, and effect is probably due to 2'amino on C3 and/or C15.2) (Pieken, 91). Phosphate—5' phosphate can be phosphorothioate (Shimayama, 93)

U4

Sugar—2'OH group can be modified. 2'H (Yang, 92), 2'F (Pieken, 91; Heidenreich, 92), 2'amino (Pieken, 91), 2'-C-allyl (Usman, 95), 2'-O-allyl (but keep as 2'OH if A6 is 2'-O-allyl) (Paolella, 92) are modifications that permit cleavage. Phosphate—5' phosphate can be phosphorothioate (Shimayama, 93)

G5

Base—2-amino group on G base is essential (cannot be inosine) (Oddi, 90; Fu, 92) Sugar—cannot make modifications to 2'OH of G5. Cannot have 2'H (Perreault, 90; Perreault, 91; Fu, 92; Williams, 92), 2'amino (Pieken, 91; Williams, 92), 2'-O-methyl (Paolella, 92), 2'F (Williams, 92).

A6

Base—can be purine (i.e. 6-amino group is not essential) (Fu, 92). N7 cannot be C7 in A base (Fu, 92). Sugar—2'OH group can be modified. 2'H (Perreault, 90; Olsen, 91; Yang, 92; Fu, 92), 2'F (Olsen, 91), 2'-O-allyl (but only if U4 is 2'H) (Paolella, 92) are modifications that permit cleavage.

N7

Seems to be a sensitive site for pyrimidine endonucleases; protection achieved if rN is rG or rA (Shimayama, 93). Sugar—2'OH group can be modified. 2'H (tested dT) (Yang, 92), 2'F (Pieken, 91; Heidenreich, 92), 2'-amino (Pieken, 91), 2'-O-allyl (Paolella, 92), 2'-O-Methyl (Usman, 95) are all modifications that permit cleavage. 3' phosphate can be phosphorothioate (has been tested for N=U) (Shimayama, 93).

G8

Sugar—cannot make modifications to 2'OH of G8. Cannot have 2'H (Fu, 92; Williams, 92; Yang, 92), 2'F (Williams, 92), 2'amino (Williams, 92), 2'-O-allyl (Paolella, 92). (Perreault (91) says can have 2'H, but Yang (92) says this site is critical if lots of other conserved nucleotides are DNA.) Phosphate—5' phosphate probably can be phosphorothioate (see N7 phosphate).

A9

Sugar—2'OH group can be modified. 2'H (Olsen, 91; Fu, 92; but Perreault (91) says cannot be 2'H), 2'F (Olsen, 91; Pieken, 91), 2'-O-allyl (Paolella, 92), 2'-O-Methyl (Usman, 95) are all modifications that permit cleavage. Phosphate—5' phosphate cannot be phosphorothioate (Buzayan, 90; Ruffner, 90). 3' phosphate can be phosphorothioate (Shimayama, 93).

G12

Base—2-amino group is essential (cannot be inosine) (Slim, 92). Sugar—2'OH group can tolerate some modifications. 2'H (Perreault, 91; Yang, 92; Williams, 92), 2'amino (Pieken, 91; Williams, 92) are OK. Cannot be 2'F (Williams, 92), 2'-O-allyl (Paolella, 92). Phosphate—5' phosphate can be phosphorothioate (Shimayama, 93).

A13

Base—Can change N7 to C. in A base (Fu, 92). 6-amino group essential (cannot be purine) (Slim, 92). Sugar—2'OH group can tolerate some modifications. 2'H (Perreault, 91; Yang, 92), 2'-O-allyl (Paolella, 92), 2'-O-Methyl (Usman, 95) are modifications that permit cleavage. Cannot have 2'F if each of A13, A14, A15.1 have 2'F (Pieken, 91). Phosphate—5' phosphate cannot be phosphorothioate (Ruffner, 90).

A14

Base—Can change N7 to C. (Fu, 92). Can be purine (Slim, 92). Sugar—2'OH group can tolerate some modifications. 2'H (Perreault, 91; Yang, 92), 2'-O-allyl (Paolella, 92), 2'-O-Methyl (Usman, 95) are modifications that permit cleavage. Cannot have 2'F if each of A13, A14, A15.1 have 2'F (Pieken, 91). Phosphate—5' phosphate cannot be phosphorothioate (Ruffner, 90).

A15.1

Base—Can change N7 to C. (Fu, 92). 6-amino group essential (cannot be purine) (Slim, 92). Sugar—Cannot modify 2° CH. Cannot have 2'H (Yang, 92), 2'-O-allyl (Paolella, 92), 2'F (if A13 and A14 also are 2'F) (Pieken, 91).

N15.2

Sugar—selected modifications permit cleavage. 2'F (Pieken, 91; Heidenreich, 92), 2'-O-allyl (Paolella, 92), 2'-O-Methyl (Usman, 95) are modifications that permit cleavage. Rates are low if 2'H (Yang, 92). Possibly cannot have 2'amino modification (several Cs in ribozyme had 2'amino modification which resulted in reduction in activity, and effect is probably due to C3 and/or C15.2) (Pieken, 91). 3' phosphate can be phosphorothioate (Shimayama, 93)

Modifications at the 3' End of an Oligonucleotide or Ribozyme

3'MEA(methoxyethylamine)phosphoramidate in last two (or last) internucleotide linkages; 3'-3' inverted diester linkage or 3'-3' inverted phosphoramidate (Shaw, 91). 3'-3' inverted Thymidine, or 3'-3' linked abasic ribose (Usman, 95).

Any combination of the above listed nucleotide modifications, substitutions, or derivatizations, made at the level of the sugar, base, or monophosphate groupings or phosphodiester linkages may be made in the compounds provided that endonuclease activity is not lost.

The compounds of this invention may be incorporated and expressed in cells as a part of a DNA or RNA transfer vector, or a combination thereof, for the maintenance, replication and transcription of the ribozyme sequences of this invention.

Nucleotide sequences encoding the compounds of this invention may be integrated into the genome of a eukaryotic or prokaryotic host cell for subsequent expression (for example as described [Sambrook, 1989]. Genomic integration may be facilitated by transfer vectors which integrate into the host genome. Such vectors may include nucleotide sequences, for example of viral or regulatory origin, which facilitate genomic integration. Methods for the insertion of nucleotide sequences into a host genome are described for example in Sambrook et al. and Hogan et al. [Sambrook, 1989; Hogan, 1986; 1989].

Nucleic acid sequences encoding the ribozymes of this invention integrated into the genome may preferably include promoter and enhancer elements operably linked to the nucleotide sequence encoding the ribozyme of this invention, with an appropriate termination sequence and capable of expressing said ribozyme in a eukaryotic (such as animal or plant cells) or prokaryotic (such as bacteria) host cells. Ideally, the promoter and enhancer elements are designed for expression in a tissue and/or developmentally specific manner.

Additionally, the compounds of the present invention may be prepared by methods known per se in the art for the synthesis of RNA molecules. (For example, according to recommended protocols of Promega, Madison, Wis., USA). In particular, the ribozymes of the invention may be prepared from a corresponding DNA sequence (DNA which on transcription yields a ribozyme, and which may be synthesized according to methods known per se in the art for the synthesis of DNA) operably linked to an RNA polymerase promoter such as a promoter for T3 or T7 polymerase or SP6 RNA polymerase. A DNA sequence corresponding to a ribozyme of the present invention may be ligated into a DNA transfer vector, such as plasmid or bacteriophage DNA. Where the transfer vector contains an RNA polymerase promoter operably linked to DNA corresponding to a ribozyme, the ribozyme may be conveniently produced upon incubation with an RNA polymerase. Ribozymes may, therefore, be produced in vitro by incubation of RNA polymerase with an RNA polymerase promoter operably linked to DNA encoding a ribozyme, in the presence of ribonucleotides and an appropriate buffer. In vivo, prokaryotic or eukaryotic cells (including mammalian, plant and yeast cells) may be transfected with an appropriate transfer vector containing genetic material encoding a ribozyme in accordance with the present invention, operably linked to an RNA polymerase promoter such that the ribozyme is transcribed in the host cell. Transfer vectors may be bacterial plasmids or viral (RNA and DNA) or portion thereof. Nucleotide sequences corresponding to ribozymes are generally placed under the control of strong promoters such as, the lac, SV40 late, SV40 early, metallothionein, or lambda promoters. Particularly useful are promoters regulated in a tissue or a temporal (developmental) specific manner or tightly regulated inducible promoter suitable for gene theory, which may be under the control of exogenous chemicals. The vector may be an adenovirus or an adeno-associated virus. See for example PCT International Publication No. WO 93/03769, "Adenovirus Mediated Transfer of Genes to the Gastrointestinal Tract", U.S. Ser. No. 747, 371; PCT International Publication No. WO 94/11506, "Adenovirus-Mediated Gene Transfer to Cardiac and Vascular Smooth Muscle," J. Leiden et al., U.S. Ser. No. 07/977,496; PCT International Publication No. WO 94/11522, "Vector for the Expression of Therapy-Relevant Genes," U. Stein et al., PCT International. Publication No. WO 94/11524, "Targetable Vector Particles," W. Anderson et al., U.S. Ser. No. 973,307; PCT International Publication No. WO 94/17832, "Targeting and Delivery of Genes and Antiviral Agents into Cells by the Adenovirus Penton," G. Nemerow et al., U.S. Ser. Nos. 08/046,159 and 08/015,225. Ribozymes may be directly transcribed in vivo from a transfer vector, or alternatively, may be transcribed as part of a larger RNA molecule. For example, DNA corresponding to ribozyme sequences may be ligated into the 3' end of a reporter gene, for example, after a translation stop signal. Larger RNA molecules may help to stabilize the ribozyme molecules against nuclease digestion within cells. On translation the reporter gene may give rise to a protein, possibly an enzyme whose presence can be directly assayed.

The compounds of this invention may be involved in gene therapy techniques, where, for example, cells from a human suffering from a disease, such as HIV, are removed from a patient, treated with the ribozyme or transfer vector encoding the ribozyme to inactivate the infectious agent, and then returned to the patient to repopulate a target site with resistant cells, so called ex vivo therapy. In the case of HIV, nucleotide sequences encoding ribozymes of this invention capable of inactivating the HIV virus may be integrated into the genome of lymphocytes or may be expressed by a non-integrating vector such as adenovirus. Such cells would be resistant to HITV infection and the progeny thereof would also confer such resistance.

A transfer vector such as a bacterial plasmid or viral RNA or DNA or portion thereof, encoding one or more of the compounds, may be transfected into cells of an organism in vivo [See for example: Llewellyn, 1987; Hanahan, 1983]. Once inside the cell, the transfer vector in some cases may replicate and be transcribed by cellular polymerases to produce ribozyme RNAs which may have ribozyme sequences of this invention; the ribozyme RNAs produced may then inactivate a desired target ANA. Alternatively, a transfer vector containing one or more ribozyme sequences may be transfected into cells by electroporation, PEG, high velocity particle bombardment or lipofectants, or introduced into cells by way of micromanipulation techniques such as microinjection, such that the transfer vector or a part thereof becomes integrated into the genone of the host cell. Transcription of the integrated genetic material gives rise to ribozymes, which act to inactivate a desired target RNA.

Transfer vectors expressing ribozymes of this invention may be capable of replication in a host cell for stable expression of ribozyme sequences. Alternatively, transfer vectors encoding ribozyme sequences of this invention may be incapable of replication in host cells, and thus may result in transient expression of ribozyme sequences. Methods for the production of DNA and RNA transfer vectors, such as plasmids and viral constructs are well known in the art and are described for example by Sambrook et al. [Sambrook, 1989].

Transfer vectors would generally comprise the nucleotide sequence encoding the ribozyme of this invention, operably linked to a promoter and other regulatory sequences required for expression and optionally replication in prokaryotic and/or eukaryotic cells. Suitable promoters and regulatory sequences for transfer vector maintenance and expression in plant, animal, bacterial, and other cell types are well known in the art and are described for example in Hogan [Hogan, 1986; 1989].

The ribozymes of the present invention have extensive therapeutic and biological applications. For example, disease causing viruses in man and animals may be inactivated by administering to a subject infected with a virus, a ribozyme in accordance with the present invention adapted to hybridize to and cleave specific RNA transcripts of the virus. Such ribozymes may be delivered by parenteral or other means of administration. Alternatively, a subject infected with a disease causing virus may be administered a non-virulent virus such as vaccinia or adenovirus which has been genetically engineered to contain DNA corresponding to a ribozyme operably linked to an RNA promoter, such that the ribozyme is transcribed in the cells of the host animal, transfected with the engineered virus, to effect cleavage and/or inactivation of the target RNA transcript of the disease causing virus.

The ribozymes of the present invention have particular application to viral diseases caused for example, by the herpes simplex virus (HSV) or the AIDS virus (HIV). Further examples of human and animal disease which may be treated with the ribozymes of this invention include psoriasis, cervical preneoplasia, papilloma disease, bacterial and prokaryotic infection, viral infection and neoplastic conditions associated with the production of aberrant RNAs such as occurs in chronic myeloid leukemia. Diseases or infections which may be treated in plants with ribozymes of this invention include fungal infection, bacterial infections (such as Crown-Gall disease) and disease associated with plant viral infection. Of particular interest would be compounds targeting genes associated with male gametophyte development. Examples include PCT International Publication No. WO 92/18625, entitled "Male-Sterile Plants, Method For Obtaining Male-Sterile Plants And Recombinant DNA For Use Therein"; U.S. Pat. No. 5,254,802, entitled "Male Sterile Brassica Plants," S. Hoekstra et al.; PCT International Publication No. WO 93/25695, entitled "Maintenance of Male-Sterile Plants," M. Williams et al., claiming the priority of U.S. Ser. Nos. 07/970,840 and 07/899,072; PCT International Publication No. WO 94/25593, entitled "Method For Obtaining Male-Sterile Plants" Stiekema et al.; PCT International Publication No. WO 94/29465, entitled "Process For Generating Male Sterile Plants" Dirks et al.

The period of treatment would depend on the particular disease being treated and could be readily determined by a physician or by a plant biologist as appropriate. Generally treatment would continue until the disease being treated was ameliorated.

The ribozymes of the present invention also have particular application to the inactivation of RNA transcripts in bacteria and other prokaryotic cells, plants, animals and yeast cells. In bacteria, RNA transcripts of, for example, bacteriophage, (which cause bacterial cell death) may be inactivated by transfecting a cell with a DNA transfer vector which is capable of producing a ribozyme in accordance with the present invention which inactivates the phage RNA. Alternatively, the ribozyme itself may be added to and taken up by the bacterial cell to effect cleavage of the phage RNA. Similarly, eukaryotic and prokaryotic cells in culture may, for example, be protected from infection or disease associated with mycoplasma infection, phage infection, fungal infection and the like.

RNA transcripts in plants may be inactivated using ribozymes encoded by a transfer vector such as the Ti plasmid of *Acrobacterium tumefaciens*. When such vectors are transfected into a plant cell and integrated, the ribozymes are produced under the action of RNA polymerase and may effect cleavage of a specific target RNA sequence. Endogenous gene transcripts in plants, animals or other cell types may be inactivated using the compounds of the present invention. Accordingly, undesirable phenotypes or characteristics may be modulated. It may, for example, be possible using the ribozymes of the present invention to remove stones from fruit or treat diseases in humans which are caused by the production of a deleterious protein, or over production of a particular protein. The compounds described above may be used to effect male sterility by destroying the pollen production in a plant. Furthermore, for the in vivo applications of the ribozymes of this invention in humans, animals, plants, and eukaryotic and prokaryotic cells, such as in phenotypic modification and the treatment of disease, it is necessary to introduce the ribozyme into cells whereafter, cleavage of target RNAs takes place. In vivo applications are highly suitable to the compounds as discussed herein.

Methods for the introduction of RNA and DNA sequences into cells, and the expression of the same in prokaryotic and eukaryotic cells are well known in the art for example as discussed by Cotten and Friedman [Cotten, 1990; Friedman, 1989]. The same widely known methods may be utilized in the present invention.

The compounds of this invention may be incorporated into cells by direct cellular uptake, where the ribozymes of this invention would cross the cell membrane or cell wall from the extracellular environment. Agents may be employed to enhance cellular uptake, such as liposomes or lipophilic vehicles, cell permeability agents, such as dimethylsulfoxide, and the like.

The compounds of the present invention may be combined with pharmaceutically and veterinarally acceptable carriers and excipients which are well known in the art, and include carriers such as water, saline, dextrose and various sugar solutions, fatty acids, liposomes, oils, skin penetrating agents, gel forming agents and the like, as described for example in Remington's Pharmaceutical Sciences, 17th Edition, Mack Publishing Co., Easton, Pa., Edited by Ostol et al., which is incorporated herein by reference.

Agriculturally acceptable carriers and excipients are well known in the art and include water; surfactants; detergents; particularly biodegradable detergents; talc; inorganic and/or organic nutrient solutions; mineral earths and clays; calcium carbonate; gypsum; calcium sulfate; fertilizers such as ammonium sulfate, ammonium phosphate, urea, carborundum, and *Agrobacterium tumefaciens*; and natural products of vegetable origin such as, for example, grain, meals and flours, bark meals; and the like.

The compounds of this invention may be provided in a composition with one or more anti-viral, anti-fungal, anti-bacterial, anti-parasitic, anti-protazoan or antihelminthic agents, herbicides, pesticides or the like, for example as described in the Merck Index (1989) 11th Edition, Merck & Co. Inc.

By way of example only, therapeutic compositions of this invention may be directed against Herpes Simplex virus types 1 and 2, psoriasis, cervical preneoplasia, papilloma disease, and bacterial and prokaryotic infection. Such treatments may, for example, involve topical application of ribozyme to the site of disease. For example, in the treatment of Herpes virus lesions, ribozymes may be formulated into a cream containing a concentration of 0.1 nM to 100 mM ribozyme, preferably 1 nM to 1 mM. The cream may then be applied to the site of infection over a 1 to 14 day period in order to cause amelioration of symptoms of the infection. Prior to the final development of topical formulations for the treatment of virus infection, effectiveness and toxicity of the ribozymes and formulations involving them may, for example, be tested on an animal model, such as scarified mouse ear, to which virus particles, such as $2 \times 10^6$ plaque forming units are added. A titer of infectious virus particles in the ear after treatment can then be determined to investigate effectiveness of treatment, amount of ribozyme required and like considerations. Similar investigations in animal models prior to human trials may also be conducted, for example, in respect of the treatment of psoriasis, papilloma disease, cervical preneoplasia, and in diseases such as HIV infection, bacterial or prokaryotic infection, viral infection and various neoplastic conditions, which neoplastic conditions involve a deleterious RNA species.

Compositions for topical application are generally in the form of creams, where the ribozymes of this invention may be mixed with viscous components. The compounds of this invention may be incorporated into liposomes or other barrier type preparations to shield the ribozymes from nuclease attack or other degradative agents (such as nucleases and adverse environmental conditions such as UV light).

Compositions may be provided as unit dosages, such as capsules (for example gelatin capsules), tablets, suppositories and the like. Injectable compositions may be in the form of sterile solutions of ribozyme in saline, dextrose or other media. Compositions for oral administration may be in the form of suspensions, solutions, syrups, capsules, tablets and the like. Ribozymes may also be provided in the form of an article for sustained release, impregnated bandages, patches and the like. The compounds of this invention may be embedded in liposomes or biodegradable polymers such as polylactic acid. Pharmaceutical compositions which may be used in this invention are described, for example, in Remington's Pharmaceutical Sciences, see above.

The present invention is further directed to a plant DNA expression cassette comprising a gene sequence flanked by promoter and terminator sequences at its 5'- and 3'ends respectively wherein said genetic science on expression provides a ribozyme RNA. The DNA cassette may further be part of a DNA transfer vector suitable for transferring the DNA cassette into a plant cell and insertion into a plant genome. In a most preferred embodiment of the present invention, the DNA cassette is carried by broad host range plasmid and which is capable of transformation into plant cells using Aarobacterium comprising Ti DNA on the left and right borders, a selectable marker for prokaryotes, a selectable marker for eukaryotes, a bacterial origin of replication and optional plant promoters and terminators such as pGA470. The present invention also includes other means of transfer such as genetic bullets (e.g. DNA-coated tungsten particles, high-velocity micro projectile bombardment) and electroporation amongst others [Maliga, 1993; Bryant, 1992; or Shimamoto, 1989].

The present invention is also directed to a transgenic plant resistant to a virus, its genome containing a sequence which gives rise, on transcription, to the nucleic acid molecule mentioned above. This transgenic plant, including fruits, and seeds thereof, may be from alfalfa, apple, arabidopsis, barley, bean, canola (oilseed rape), cantaloupe, carnation, cassava, casuarina, clover, corn, cotton, courgette, cucumber, eucalyptus, grape, melon, papaya, pepper, potato, rice, rose, snap dragon, soybean, squash, strawberry, sunflower, sweet pepper, tobacco, tomato, walnut, wheat or zucchini. Also included are the plant cells transformed by the above-mentioned transfer vector, as well as a prokaryotic, eukaryotic or yeast, plant or animal cell, comprising a nucleotide sequence which is, or on transcription gives rise to, the nucleic acid molecule.

The present invention will now be illustrated by way of non-limiting Examples only, with reference to the following non-limiting Examples, and Figures.

EXAMPLE 1

Minizymes containing the deoxyribonucleotides d(GTTTT) and d(GTTT7'T) between the conserved nucleotides $A_9$ and $G_{12}$ offer the following advantages:
(i) These minizymes show fast cleavage rates in vitro. See following data for the test systems Interleukin-2, TAT, CAT, and TNFα.
(ii) The CAT minizyme (CATMgtttt) shows activity against CAT in CHO cells (see Example 2).
(iii) The IL2 minizyme (IL2Mgtttt) shows activity against Interleukin-2 in PBMN cells (see Experiment 3)(Seq ID No. 5).

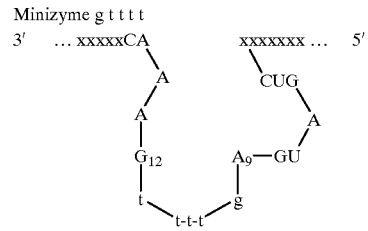

1. Method for determining rates of cleavage ($k_{obs}$) by minizymes.

In these experiments, conditions are optimized so that the rate-limiting step in the reaction is cleavage of the substrate. The substrate consists of only a small number of nucleotides, in order to prevent strong self-association, and hence substrate association with the minizyme is not rate-limiting. In addition, the minizyme concentration is at least two-fold greater than substrate concentration, which is high enough to ensure all substrate molecules are bound by minizymes. Thus, the measured rate in these experiments should be rate of cleavage of the substrate.

The substrate is labelled on its 5' end with [$^{32}$P]-phosphate. In general, the minizyme and substrate are heated together in buffer for two minutes at 80° C. without magnesium, in order to denature the nucleic-acid molecules; however, this step has been shown not to be necessary in a number of cases. The cleavage reaction is initiated by adding Mg$^{++}$ to the mixture at 37° C. [MgCl$_2$]=10 mM, [Tris.HCl buffer]=50 mM, [Minizyme]=5 μM (typically), [Substrate]=2 μM (typically), temperature=37° C., pH 8.2 (for Interleukin-2 and TAT systems) and pH 8.0 (for CAT and TNFα systems). Samples are taken from the reaction mixture at various times, and the reaction is stopped by adding excess EDTA and formamide. The samples are electrophoresed on a polyacrylamide gel containing 7M urea, and the amounts of 5'-product and uncleaved substrate are quantified using a PhosphorImager (Molecular Dynamics) and ImageQuant software. Kinetic parameters are obtained by fitting the data for % of product formed ($P_t$) versus time (t) to the equation $$P_t = P_\infty - (\exp(-k_{obs}t)P_A)$$

where $P_t$ is the amount of product at time t, $P_\infty$ is the amount of product at t=∞, $k_{obs}$ is the first-order rate-constant for the reaction, and $P_A$ is the difference between the percentage of product at t=∞ and t=0. This is a conventional first-order kinetic equation from which $k_{obs}$, $P_\infty$, and $P_A$ are determined by least-squares fitting of the data.

2. Sequences of molecules

Upper-case letters represent ribonucleotides, lower-case letters represent deoxyribonucleotides.

Interleukin-2 system. (Seq ID No. 6–10)
Substrate (15-mer)

5′ UCCUGUC UGCAUUg 3′

Minizyme g t t t t

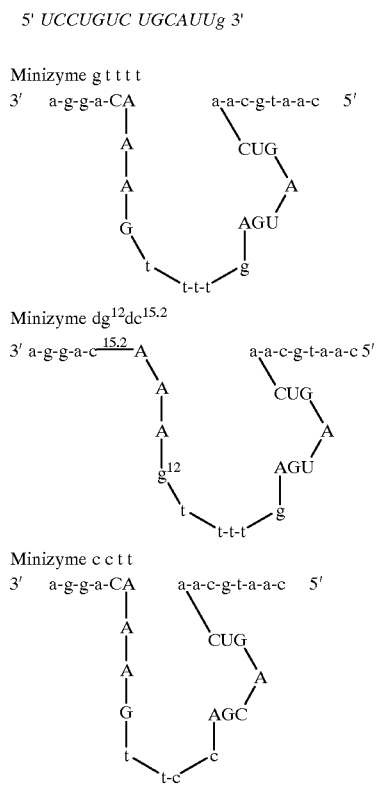

Minizyme dg$^{12}$dc$^{15.2}$

Minizyme c c t t

Other interleukin-2 minizymes. "x" represents the deoxyribonucleotides forming the linker between the ribonucleotides. The various sequences of "x" that have been tested appear in the following table (Table 1).

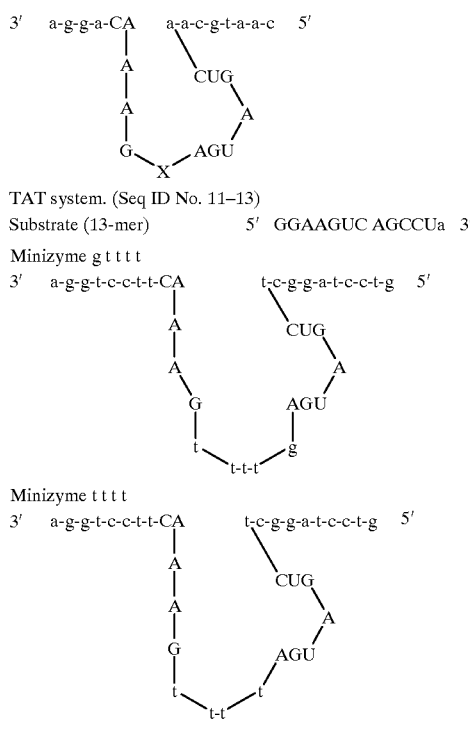

TAT system. (Seq ID No. 11–13)
Substrate (13-mer)          5′ GGAAGUC AGCCUa 3′
Minizyme g t t t t Minizyme t t t t -continued CAT system. (Seq ID No. 14–17)
Substrate (17-mer)          5′ UUCCAUGUC GGCAGAAt 3′

Minizyme g t t t t

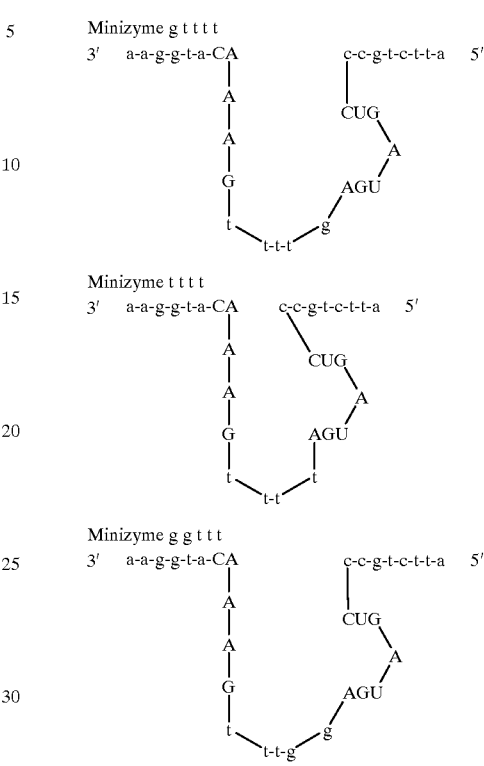

Minizyme t t t t

Minizyme g g t t t

Tumor Necrosis Factor α(TNFα) system. (Seq ID No. 18–20)
Substrate (20-mer)          5′ CCAGGCAGUC AGAUCAUCUt 3′

Minizyme g t t t t

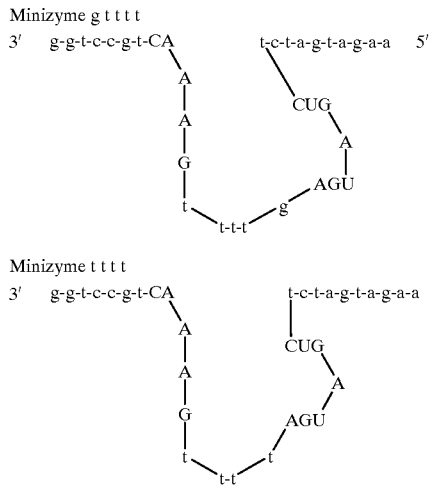

Minizyme t t t t

3. Observed cleavage rate ($k_{obs}$ min$^{-1}$) and extent of cleavage (%P) of short substrates by minizymes with various linkers. ("Table 1B)".

Experimental conditions: 10 mM MgCl$_2$, 50 mM Tris.HCl, pH 8.2 (for Interleukin-2 and TAT systems) and pH 8.0 (for CAT and TNFα systems), 37° C., [Substrate]=2 μM, [Minizyme]=5 μM (except [TNCMtttt, TNFMgtttt]=4.3 μM).

| Minizyme linker | Expt. 1 $k_{obs}$ | % $P_\infty$ | Expt. 2 $k_{obs}$ | % $P_\infty$ | Expt. 3 $k_{obs}$ | % $P_\infty$ | Mean $k_{obs}$ | ($\sigma$) | % $P_\infty$ | ($\sigma$) |
|---|---|---|---|---|---|---|---|---|---|---|
| Interleukin-2 | | | | | | | | | | |
| 5' × 3' | | | | | | | | | | |
| cctt | 0.010 | 80# | 0.011 | 80# | | | 0.011 | (.001) | 80# | |
| tttt | | | 0.052 | 81.1 | 0.049 | 84.2 | 0.051 | (.002) | 83 | (2) |
| ttttt | | | 0.058 | 86.1 | 0.064 | 82.1 | 0.061 | (.004) | 84 | (3) |
| ttttc | 0.016 | 76.3 | 0.015 | 80.0 | | | 0.016 | (.001) | 78 | (3) |
| gttt | 0.118 | 82.3 | 0.107 | 84.5 | | | 0.113 | (.008) | 83 | (2) |
| gtttt | 0.299 | 83.5 | 0.287 | 85.3 | 0.225 | 84.9 | 0.270 | (.040) | 85 | (1) |
| gttttt | 0.287 | 82.4 | 0.253 | 84.1 | | | 0.270 | (.024) | 83 | (1) |
| gtttttt | 0.200 | 84.3 | 0.169 | 88.6 | | | 0.185 | (.022) | 86 | (3) |
| gttta | 0.026 | 85.9 | 0.022 | 94.7 | | | 0.024 | (.003) | 90 | (6) |
| gtttta | 0.047 | 81.0 | 0.038 | 88.4 | | | 0.043 | (.006) | 85 | (5) |
| gtttg | 0.122 | 82.3 | 0.092 | 89.8 | 0.107 | 83.9 | 0.107 | (.015) | 85 | (4) |
| gttttg | 0.101 | 82.1 | 0.094 | 84.2 | | | 0.098 | (.005) | 83 | (2) |
| ggttt | 0.049 | 82.4 | 0.048 | 89.4 | | | 0.049 | (.001) | 86 | (5) |
| gtgtt | 0.178 | 83.0 | 0.181 | 83.2 | | | 0.180 | (.002) | 83 | (1) |
| gttgt | 0.065 | 93.9 | 0.072 | 85.3 | | | 0.069 | (.005) | 90 | (6) |
| gtttt (dg$^{12}$dc$^{15.2}$) | 0.041 | 90.0 | 0.040 | 91.7 | | | 0.041 | (.001) | 91 | (1) |
| TAT | | | | | | | | | | |
| tttt | 0.074 | 89.1 | 0.067 | 91.9 | | | 0.071 | (.005) | 91 | (2) |
| gtttt | 0.179 | 89.7 | 0.190 | 90.8 | | | 0.185 | (.008) | 90 | (1) |
| CAT | | | | | | | | | | |
| tttt | 0.186 | 82.9 | 0.175 | 84.7 | | | 0.181 | (.008) | 84 | (1) |
| gtttt^ | 0.526* | 60.8 | 0.448* | 63.8 | 0.478* | 62.8 | 0.48* | (0.04) | 62 | (2) |
| gtttt^ | 0.791* | 72.0 | 0.809* | 71.4 | | | 0.80* | (0.01) | 72 | (1) |
| gtttt^ | 0.650* | 63.0 | | | | | | | | |
| gtttt^ | 0.453* | 61.0 | | | | | | | | |
| gtttt^^ | | | | | | | 0.59* | (0.16) | 65 | (5) |
| ggttt | 0.278* | 68.8 | 0.352* | 67.6 | | | 0.32* | (0.05) | 68 | (1) |
| TNFα | | | | | | | | | | |
| tttt | 0.002 | 70.0# | 0.002 | 70.0# | | | 0.002 | (.001) | 70.0# | |
| gtttt | 0.274 | 59.0 | 0.180 | 74.2 | 0.303 | 58.7 | 0.25 | (0.06) | 64 | (9) |

\# fixed at this value.
^ four different syntheses, ^^ average of data for the four syntheses.
*reaction is biphasic; rate constant for the initial faster reaction is given.

4. Minizymes with 5'd(GTTTT) linkers have improved cleavage activity in vitro compared with those with 5'd (TTTT) linkers.

TABLE 2

| System | $k_{obs}$ (Mgtttt) | $k_{obs}$ (Mtttt) | $k_{obs}$ (Mgtttt)/$k_{obs}$(Mtttt) |
|---|---|---|---|
| Interleukin-2 | 0.270 | 0.051 | 5.3 |
| TAT | 0.185 | 0.071 | 2.6 |
| CAT | 0.59 | 0.181 | 3.3 |
| TNFα | 0.25 | 0.002 | 125 |

The data in table 2 show that the minizymes with gtttt linkers consistently show $k_{obs}$ values of 0.2 min$^{-1}$ or better. Since we know that IL2Mgtttt, with $k_{obs}$=0.27 min$^{-1}$, is active in cells (see Example 3), we can conclude that a minizyme with at least this level of activity in an in vitro system should not be hindered in cells by its $k_{obs}$ value (i.e. rate of cleavage should not be rate limiting in cells), all other things being equal (such as target site being accessible).

EXAMPLE 2

Minizyme Suppression of CAT Expression in CEO Cells

Introduction

Minizymes are sequence specific RNA endonucieases derived from standard hammerhead ribozymes by elimination of helix II. Minizymes have been shown to exhibit significant in vitro cleavage activity against both short RNA targets as well as long transcribed RNA. This report describes the testing of a particular minizyme targeted against the mRNA of CAT (Chloramphenicol acetyl transferase) expressed in a mammalian cell line. The minizyme is a chimeric DNA/RNA molecule synthesized by solid phase methods and transfected into a CHO (chinese hamster ovary) cell line stably expressing CAT.

Experimental Protocol

A CHO based CAT expressing cell line MC 11, in which CAT is expressed from the Human metallothionein IIA(MT) promoter, was used in all experiments. The MT promoter is transcriptionally active at very low metal concentration and a reasonable level of CAT expression is observed in the absence of induction by added metals.

8×10$^4$ cells were plated out in EMEM containing 10% foetal calf serum and allowed to attach overnight (14–16 hours). The cells were washed once with 1×PBS to remove serum, then the test molecules (pre-treated for 30 minutes with 1 μL of lipofectamine (GIBCO BRL, Life Technologies, Maryland, USA) in serum-free EMEM) were transferred to the cells. The final concentration of test molecules was 10 $\mu$M. After four hours both serum and Alamar Blue (Alamar Bio-Sciences Inc, Sacramento Calif.) (each to a final concentration of 10%) was added to the cells and incubation continued for a further 18 hours. At this time the supernatant was removed and the cumulative cell metabolic activity determined by measuring the extent of reduction of the Alamar Blue reagent. The cells were harvested and CAT activity assayed (Sleigh, 1986).

Alamar Blue Assay

Alamar Blue is a commercial material designed for use in cytotoxicity assays for cells in culture. The reagent is reduced intracellularly in an energy dependent fashion. The reduced form of the reagent is readily quantified by either its absorption spectrum or by fluorescence. We have quantified the reduced form of Alamar Blue by absorption spectroscopy.

Target mRNA

The target site in the CAT mRNA corresponds to CAT site 3 described in Haseloff and Gerlach (1988). The cleavage triplet is a GUC site and is located towards the 3' end 662 nucleotides from the ATG start codon.

Sequences of Molecules

The test molecules are as follows (Seq ID No. 21–24): Lower case letters are DNA, upper case letters are RNA.

```
tRNA              Yeast tRNA (Sigma) Phenol/Chloroform extracted.

N17               5' nnn nnn nnn nnn nnn nn  3'  (n = a, g, c or t)

CAT Antisense     5' att ctg ccg aca tgg aa 3'

CAT Minizyme      5' att ctg cc CUGAUGA gtttt GAAAC atg gaa 3'

CAT Inactive Minizyme 5' att ctg cc CUGAUGA gtttt GAGAC atg gaa 3'
```

Bold G in CAT Inactive Minizyme represents the mutation that inactivates the minizyme.

Results

TABLE 3

Data from three Independent Experiments

| Treatment | Replicas | CAT Activity ± SEM | Alamar Blue ± SEM |
|---|---|---|---|
| Experiment 1' | | | |
| serum starved + lipofectamine | 3 | 9385 ± 318 | 1.08 ± 0.06 |
| Minizyme | 3 | 3788 ± 603 | 1.19 ± 0.06 |
| Antisense | 3 | 3885 ± 490 | 0.975 ± 0.05 |
| Inactive Minizyme | 3 | 7043 ± 695 | 1.085 ± 0.01 (n = 2) |
| $N_{17}$ | 3 | 7254 ± 876 | 0.966 ± 0.06 |
| Experiment 2' | | | |
| serum starved + lipofectamine | 2 | 10573 ± 455 | 1.045 ± 0.03 |
| tRNA | 3 | 9680 ± 656 | 0.938 ± 0.04 |
| Minizyme | 3 | 4943 ± 974 | 0.953 ± 0.02 |
| Antisense | 3 | 5073 ± 467 | 0.883 ± 0.01 |
| Inactive Minizyme | 3 | 6641 ± 642 | 0.872 ± 0.05 |
| $N_{17}$ | 3 | 4260 ± 342 | 0.857 ± 0.05 |
| Experiment 3' | | | |
| serum starved + lipofectamine | 2 | 4143 ± 269 | 0.89 ± 0.05 |
| tRNA | 3 | 5646 ± 235 | 0.781 ± 0.02 |
| Minizyme | 3 | 2855 ± 491 | 1.031 ± 0.07 |
| Antisense | 3 | 2978 ± 259 | 0.712 ± 0.10 |
| Inactive Minizyme | 3 | 5969 ± 225 | 0.778 ± 0.04 |
| $N_{17}$ | 3 | 2210 ± 195 | 0.767 ± 0.04 |

TABLE 4

Mean ± SEM CAT Expression as a percentage of Control.
(Controls are serum starved + lipofectamine treated cells)

| Treatment | Experiment 1 | Experiment 2 | Experiment 3 | Mean ± SEM |
|---|---|---|---|---|
| Control | 100 ± 3.3 | 100 ± 4.3 | 100 ± 6.5 | 100 |
| tRNA | — | 91.6 ± 6.8 | 136.3 ± 4.2 | 114 ± 22 |
| Minizyme | 40.4 ± 15.9 | 46.8 ± 19.7 | 68.9 ± 17.2 | 52 ± 9 |
| Antisense | 41.4 ± 12.6 | 48.0 ± 9.2 | 71.9 ± 8.7 | 54 ± 9 |
| Inactive Minizyme | 75.0 ± 9.9 | 62.8 ± 9.7 | 144.1 ± 3.8 | 94 ± 25 |
| $N_{17}$ | 77.3 ± 12.1 | 40.3 ± 8.0 | 53.3 ± 8.8 | 57 ± 11 |

Figure 2:
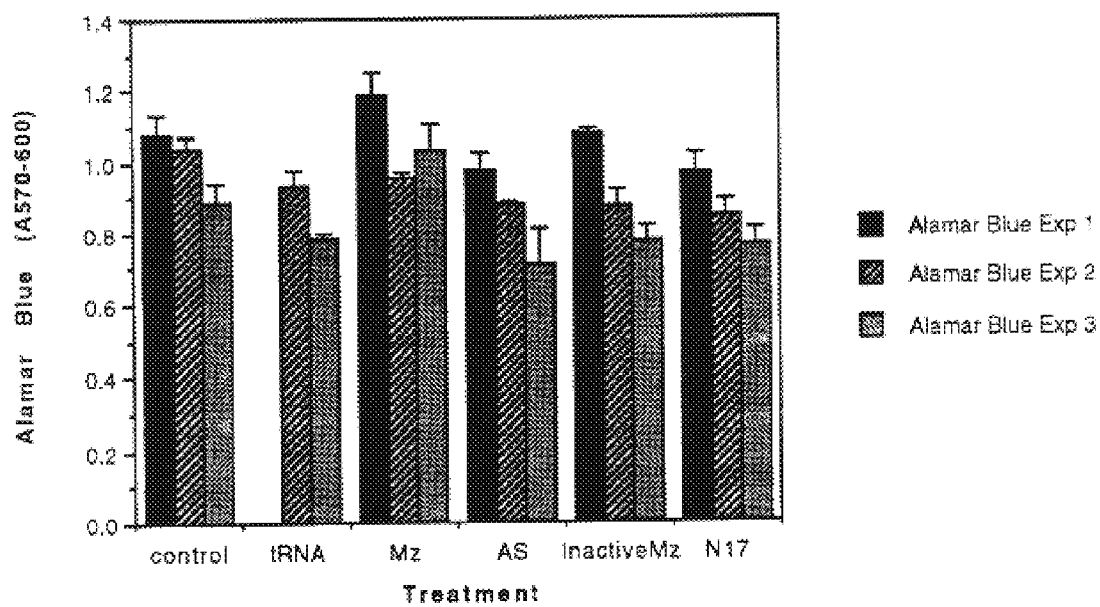
FIG. 2 shows the extent of Alamar Blue Reduction (mean±SEM) in the same experiments as in FIG. 1. Extent of reduction relates to metabolic activity of the cells during the 18 hours post-transfection.
Figure 3:
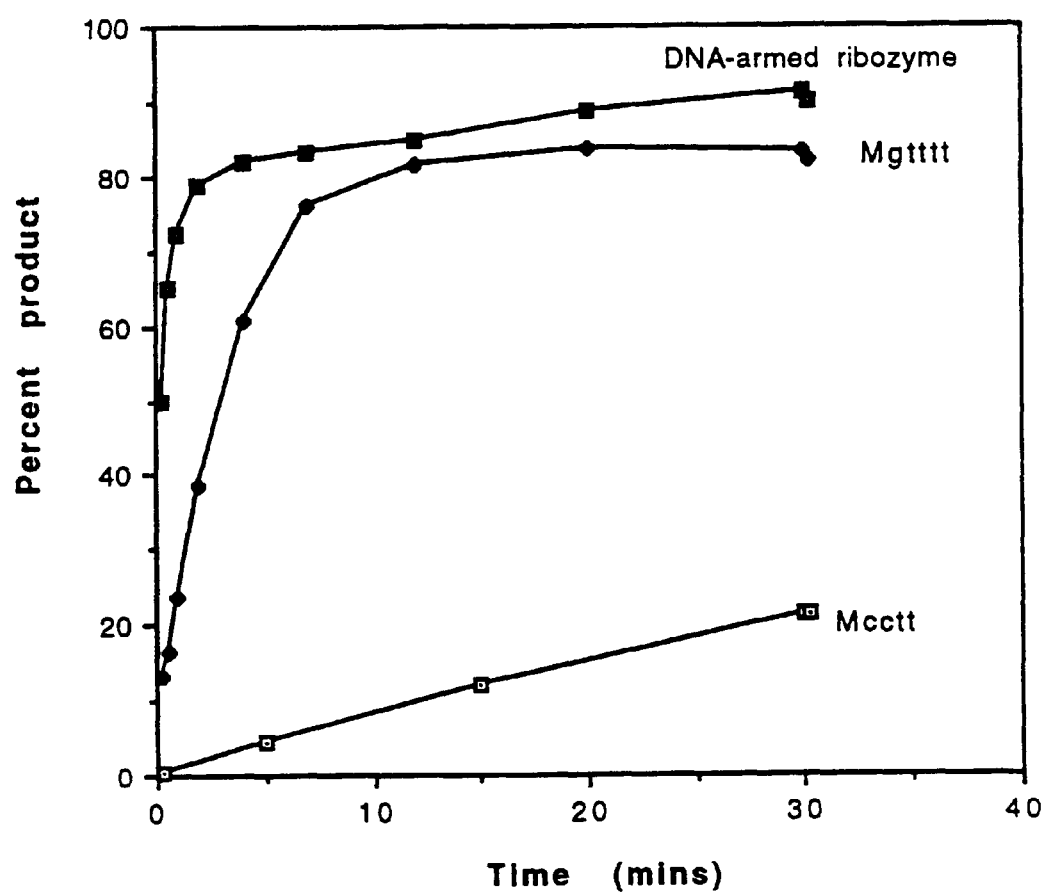
FIG. 3 shows the cleavage of the IL-2 substrate at 37° C. by minizymes (with cctt and gtttt linkers) and a ribozyme with DNA arms.
Figure 4:
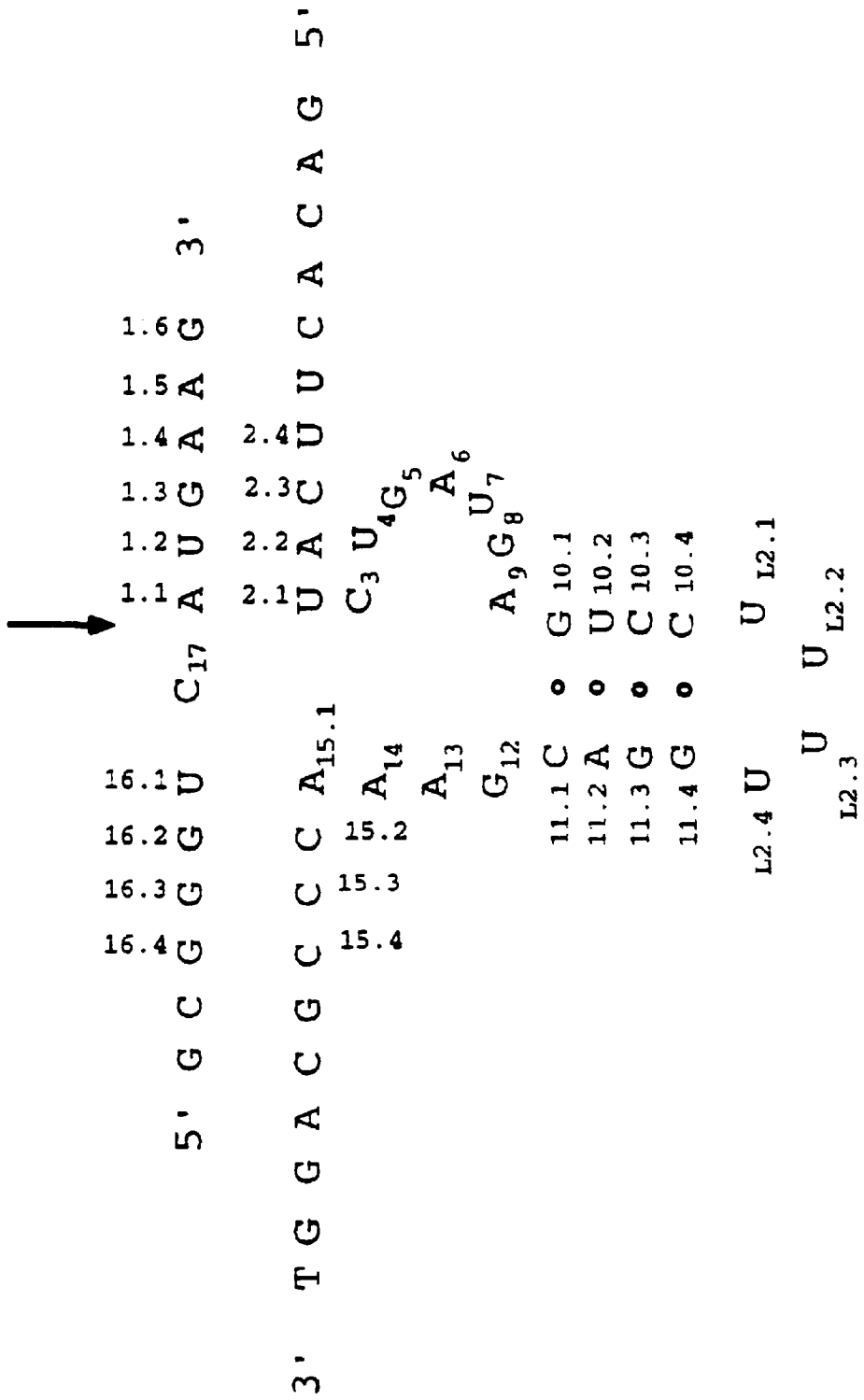
FIG. 4 shows the numbering scheme of (Hertel 1992) for a hammerhead ribozyme and its substrate (Seq ID No. 1–2).

FIG. 1 shows the CAT Expression (Mean±SEM) for Different treatments. Each experiment is performed in triplicate. FIG. 2 shows the extent of Alamar Blue Reduction (mean±SEM) in the same experiments as in FIG. 1. Extent of reduction relates to metabolic activity of the cells during the 18 hours post-transfection.

Discussion

The CAT minizyme contained the new linker 5'gtttt. When tested against a short 17-mer synthetic RNA substrate in vitro at 37° C., the minizyme cleaved the substrate with a reasonable rate constant (~0.5 min$^{-1}$, t½~1.4 minutes). In all experiments a constant number of cells (8×10$^4$) were seeded and treated identically with the exception of the added oligonucleotides. Based on observed CAT activity, the random 17-mer does no. appear to be an appropriate control molecule. Accordingly tRNA was included in two of the experiments to provide an alternative control.

The minizyme and the DNA antisense show similar levels of suppression (52±9%, 54±9%, respectively) and both are significantly more effective than the inactivated minizyme (94± 25%, mean results Table 4). Thus both the minizyme and the antisense are showing activity in this cultured cell system.

We have been mindful of the danger of selecting a single protein or mRNA level as a specificity control and have therefore monitored the rate of general metabolism (by Alamar Blue reduction) as a measure of the specificity of the test molecules. It is interesting to note that the minizyme is apparently less toxic than the antisense in all experiments (Table 3, FIG. 2). Therefore the relative activity of the minizyme may be greater than that of the antisense, since a proportion of the apparent activity of the antisense molecule could result from a reduction in cell metabolism compared with minizyme treated cells.

EXAMPLE 3

The Activities of DNA-armed Ribozymes and Minizymes Against Interleukin-2 mRNA In Vivo The Molecules Tested The following molecules (2–7) have been synthesized and tested for activity using one or more of the assays described below. Molecule 2 is a hammerhead ribozyme with deoxyribonucleotides in the arms which hybridize to the substrate. Molecule 3 is a minimized hammerhead ribozyme (minizyme) with a linker of sequence d(GTTTT) replacing stem-loop II of the full-sized ribozyme. Molecule 4 is a minizyme with 5' d(GTTTT) linker, which has been rendered inactive by replacing the conserved $A_{14}$ by a G. Molecule 5 is a DNA antisense control with sequence complementary to the 15-nucletide target sequence. Molecule 6 is a DNA control with the same base composition as the DNA antisense, but with scrambled sequence. Molecule 1 is a 15-nucleotide, synthetic substrate with the same sequence as that targeted in the IL2 m-RNA; it is used to determine cleavage rate constants for the ribozyme and minizymes in vitro. In the sequences below, ribonucleotides are denoted by upper-case letters and deoxyribonucleotides by lower-case letters (Seq ID No. 25–31).

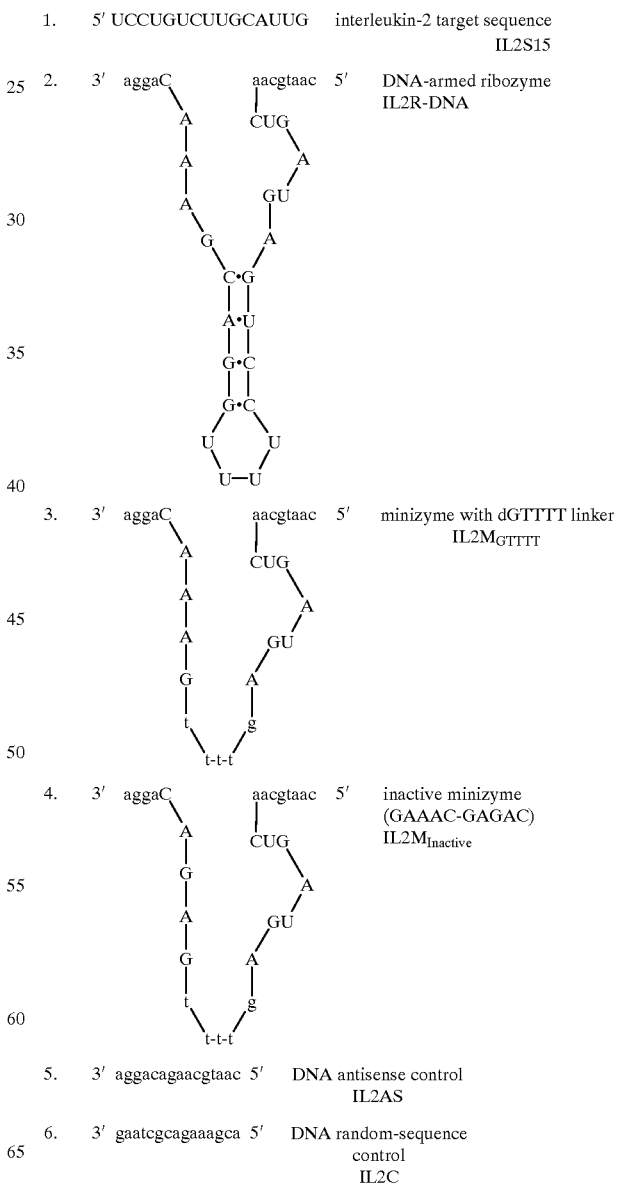

7. 3' aggaC aacgtaac 5'  minizyme with dCCTT linker
IL2M$_{CCTT}$

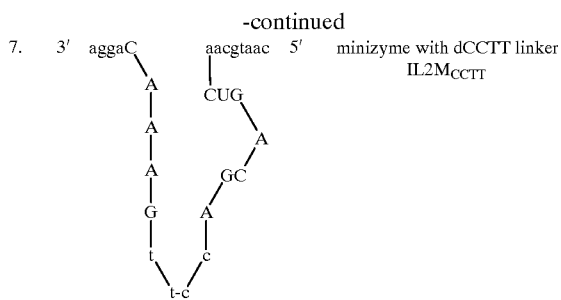

Preparation of Oligonucleotides

The oligonucleotides were synthesised on an Applied Biosystems (Foster City, Calif.) model 391 synthesiser using protected DNA phosphoramidite monomers and RNA monomers, protected at the 2'-hydroxyl by tert-butyldimethylsilyl groups, from Millipore (Marlborough, Ma.). For convenience in the syntheses, the 3' nucleotide in all molecules is a deoxyribonucleotide. The methods used for the deprotection and gel-purification of the oligonucleotides were as described previously (McCall et al., 1992), with the exception that the oligonucleotides used for testing in cells were precipitated twice (rather than once) from 0.3 M sodium acetate and 800 ethanol, and then washed twice (rather than once) in cold 80% ethanol before drying under vacuum. The oligonucleotides were re-dissolved in autoclaved, de-ionized water. The concentrations of the oligonucleotide solutions were determined by UV spectroscopy using the following molar extinction coefficients for the nucleotides at 260 nm: A 15,400, G 11,700, C 7,300, T and U 8, 800 Lmol$^{-1}$cm$^{-1}$. The purity of each oligonucleotide was checked by phosphorylating the 5' end using [$\gamma$-$^{32}$] ATP and polynucleotide kinase (Boehringer Mannheim, Germany) as described previously (McCall et al., 1992). The oligonucleotides were stored at −20° C.

Determining Rates of Cleavage (k$_{obs}$) by Minizymes

The rates at which the minizymes (IL2M$_{TTTT}$ and IL2M$_{CCTT}$) and ribozyme (IL2R-DNA) cleaved their cognate, short substrate (IL2S15) were determined in 10 mM MgCl$_2$, 50 mM Tris.HCl buffer, pH 8.25, at 37° C. with 5 µM minizyme and 2 µM substrate. The substrate was labelled on its 5' end with [$^{32}$P]-phosphate. The minizyme and substrate were heated together in buffer for two minutes at 70° C., put to 37° C. for 2 minutes, centrifuged briefly at room temperature, and then returned to 37° C. for 2 minutes before starting the reaction by adding MgCl$_2$ (at 37° C.) to the mixture. The volume of the reaction mixture was generally 30 µL. 2 µL samples were taken at various times, and the reactions in these were quenched by adding 4 µL of 20 mM EDTA, 80% formamide, 0.1% bromphenol blue and 0.1% xylene cyanol. The samples were electrophoresed on a 15% polyacrylamide gel containing 7M urea, and the amounts of 5'-product and uncleaved substrate were quantified using a Molecular Dynamics PhosphorImager (Sunnyvale, Calif.) and ImageQuant software. Kinetic parameters were obtained by fitting the data for % of product formed (P$_t$) versus time (t) to the equation $$P_t = P_\infty - (\exp(-k_{obs}t)P_A)$$

where P$_t$ is the amount of product at time t, P$_\infty$ is the amount of product at t=∞, k$_{obs}$ is the first-order rate-constant for the reaction, and P$_A$ is the difference between the percentage of product at t=∞ and t=0. This is a conventional first-order kinetic equation from which k$_{obs}$, P$_\infty$ and P$_A$ Sterile are determined by least-squares fitting of the data. The quoted rate constants are the mean (±standard deviation) of at least two experiments.

Assays for Interleukin-2

Abbreviations: PBMN (peripheral blood mononuclear cells), PHA (phytohemagglutinin), IL-2 (interleukin-2).

Interleukin-2 is synthesised and secreted by T-lymphocytes following their activation by antigens or mitogens. In experiments to determine how well the test molecules could suppress the production of IL-2, an enriched population of human PBMN T-cells were transfected with the test molecules, and then stimulated with PHA to produce IL-2. In all cases, these test molecules were co-transfected. with 1 µg tRNA and their effects on IL-2 levels were determined relative to the effect of the control which was 1 µg tRNA.. The amounts of IL-2 secreted were assayed by three methods. In one method, IL-2 was assayed indirectly by measuring the ability of the supernatant from the PBMN cells to promote the growth of IL2-dependent mouse CTLL cells. In another, since IL-2 produced by PBMN T-cells promotes the growth of the same cells, IL-2 levels were assayed directly by measuring the growth of the stimulated cells. In addition to these bio-assays, immunoassays (which measure free and receptor-bound IL-2) were performed.

Indirect Bio-assay

This assay is specific For interleukin-2 and is based on the absolute requirement of IL-2 for the growth of CTLL cells. Before use, the CTLL cells, maintained continuously proliferating in complete media containing added IL-2, were washed 3 times in complete media without added IL-2 (Tables 13a and 13b).

In microtitre trays 100,000 PBMN cells (enriched in T-cells) were transfected in complete medium (RPMI plus 10% foetal-calf serum) with the test and control molecules at 5, 10 and 20 µM using 25 kg/mL DOTAP (Boehringer Mannheim, Germany) according to the manufacturer's instructions. After a period of 7 hours, the cells were stimulated with 5 µg/mL PHA (Sigma). After an additional 15–20 hours, supernatants from the PBMN cells were serially diluted and, in triplicate, 100 µL from each dilution were added to 5000 CTLL cells in 20 µL media. The CTLL cells were allowed to grow for 20 hours, were pulsed with $^3$H-thymidine for 4 hours, were harvested, and then the DNA-associated radioactivity was determined. Slow growth of the CTLL cells (low level of incorporated $^3$H-thymidine) indicates low levels of interleukin-2 in the supernatant, and hence a test molecule with good activity against interleukin-2 in the PBMN cells. The percentage inhibition of IL-2 by the test molecules is measured in the range where the cell growth-rate is linearly dependent on the amount of IL-2 (Sioud, 1994).

Direct Bio-assay

PBMN cells were transfected with the test: molecules for 12 hours, stimulated with PHA for about 48 hours, pulsed with 2H-thymidine, and then harvested 18 hours later to determine DNA-associated radioactivity (Tables 14a and 14b).

Enzyme Amplified Sensitivity Immuno-Assay (EASIA)

Total IL-2 in the supernatant from PBMN cells transfected with 20 µM IL2M$_{GTTTT}$ and 20 µM IL2M$_{Inactive}$ was determined using IL2-EASIA, a solid-phase Enzyme Amplified Sensitivity Immuno-Assay performed in microtitre plates according to the manufacturer's instructions (MADGENIX) (Table 15).

Toxicity to Cells

The viability of PBMN cells which had been transfected with test and control molecules was determined using acridine orange and ethidium bromide. Dead cells appear orange and live cells appear green in the presence of these indicators. The assays were performed on PBMN cells that were transfected with the test and control molecules for a period of 22–27 hours; these cells were not stimulated with PHA since this results in cell aggregation and hence inaccuracy in cell counting. In parallel, cells from the same donor were transfected with the test and control molecules and stimulated with PHA, and when supernatants from these cells were collected for assaying IL-2 levels, the viabilities of the cells not stimulated by PHA were determined.

Activities of DNA-armed Ribozymes and Minizymes

The original set of molecules synthesized for testing contained the DNA-armed ribozyme, the minizyme with d(CCTT) linker, the DNA antisense, and the DNA random-sequence control (molecules 2, 7, 5 and 6 respectively). In these first experiments using the indirect assay, with transfection concentrations of test molecules at 10 $\mu$M, the DNA-armed ribozyme showed good activity against IL2, while the minizyme with d(CCTT) linker and the DNA random-sequence control showed no activity; the DNA antisense showed about 50% the activity of the DNA-armed ribozyme. The activities of the DNA-armed ribozyme and the minizyme in cells correlated with the observed cleavage-activities of these molecules as measured against the short synthetic IL2 substrate in vitro. Since the cleavage rate shown by the minizyme with d(CCTT) linker was extremely slow, we investigated the reason for this poor activity. In this investigation we found that by changing the linker from 5' d(CCTT) to 5' d(GTTTT) the cleavage rate of the minizyme could be increased 25-fold. The observed cleavage rate constants in 10 mM $MgCl_2$, at pH 8.25 and 37° C., for the DNA-armed ribozyme, the minizyme with d(CCTT) linker, and the new minizyme with d(GTTTT) linker, against their cognate, short substrate are 1.4 (0.2), 0.011 (0.001) and 0.27 (0.04) $min^{-1}$, respectively.

Following the discovery of the highly active minizyme with d(GTTTT) linker, we synthesized in large scale the DNA-armed ribozyme, the minizyme with d(GTTTT) linker, an inactivated minizyme with d(GTTTT) linker, the DNA antisense, and the DNA random-sequence control (molecules 2–6 above), and tested them for activity in cells.

Results from Independent Experiments Using Molecules 2–6

In the tables below, the effectiveness of each test molecule (at different concentrations) in inhibiting the production of IL2 is presented as % inhibition averaged over two or three independent experiments (each done in duplicate or triplicate) with standard deviations given in brackets. In the first of each pair of tables, the data show the effectiveness of the test molecules against IL2, relative to that of the DNA random-sequence control taken as having oil inhibitory effect. Since ribozymes and minizymes are being developed as alternatives to other oligonucleotide-based therapies, we believe that the inhibitory effects of these molecules, over and above the non-specific effects of a randomly-chosen oligonucleotide, are the data of interest. In most experiments, tRNA was also included as an additional control molecule. Generally, the DNA random-sequence control showed some activity against IL2 relative to tRNA, and so these data are presented for information (relative to tRNA taken as having 0% inhibitory effect) in the second of each pair of tables.

Indirect assay. % Inhibition of IL2 as measured by the indirect assay.

TABLE 13

| Test molecule | Transfection concentration | | |
|---|---|---|---|
| | 5 $\mu$M | 10 $\mu$M | 20 $\mu$M |
| Data relative to DNA random-sequence control. | | | |
| IL2R-DNA | 33 | 42 (13) | 69 (1) |
| IL2M$_{GTTTT}$ | 31 | 41 (4) | 53 (11) |
| IL2M$_{inactive}$ | 5 | 6 (27) | 28 (6) |
| IL2AS | 10 | 21 (19) | 13 (6) |
| Data relative to tRNA. | | | |
| IL2R-DNA | 45 | 51 (9) | 80 (4) |
| IL2M$_{GTTTT}$ | 43 | 51 (3) | 73 (12) |
| IL2M$_{inactive}$ | 22 | 22 (17) | 47 (12) |
| IL2AS | 25 | 35 (9) | 49 (15) |
| IL2C | 18 | 16 (7) | 35 (9) |

Direct assay. % Inhibition of IL2 as measured in individual experiments by the direct assay.

TABLE 14

| Test molecule | Transfection concentration |
|---|---|
| | 10 $\mu$M |
| Data relative to DNA random-sequence control. | |
| IL2R-DNA | 67 (3) |
| IL2M$_{GTTTT}$ | 46 (6) |
| IL2M$_{inactive}$ | 24 (2) |
| IL2AS | 28 (14) |
| Data relative to tRNA. | |
| IL2R-DNA | 73 (4) |
| IL2M$_{GTTTT}$ | 55 (7) |
| IL2M$_{INactive}$ | 37 (2) |
| IL2AS | 40 (14) |
| IL2C | 18 (4) |

EASIA

TABLE 15

| Transfection concentration 20 $\mu$M. | | |
|---|---|---|
| Test molecule | IU/ml | % inhibition relative to tRNA |
| IL2M$_{GTTTT}$ | 70 | 72% |
| IL2M$_{inactive}$ | 120 | 52% |
| control (tRNA) | 250 | — |

Summary of Results

The DNA-armed ribozyme (IL2R-DNA) and the minizyme with d(GTTTT) linker (IL2M$_{GTTTT}$) show activity specifically against interleukin-2 in human PBMN cells. The effects of these two molecules are greater than those measured for a DNA antisense molecule (IL2AS) and an inactivated minizyme (IL2M$_{Inactive}$) directed to the same target site on the IL2 mRNA, at transfection concentrations of 5, 10 and 20 $\mu$M. The molecules do not appear to be toxic to cells over a 24-hour period.

EXAMPLE 4

Mini-ribozymes

Comments in publications on hammerhead ribozymes teach that helix II can be reduced to 2 b.p. without loss of activity, but further reduction to 1 b.p. results in at least a 10-fold reduction in activity (see data from Tuschi and Eckstein (1993) and from Long and Uhlenbeck (1994)). Note that these data are for all-RNA ribozymes we have found that ribozymes with 1 b.p. in helix II, such that the sequence of "stem-loop II" is 5'GTTTC or 5'GTTTC, where T may be dT or rU, have better than 10% the activity of analogous ribozymes with 4 b.p. in helix II. We call such ribozymes "mini-ribozymes". In some cases, the mini-ribozymes have observed cleavage constants which exceed that of the full-sized analogous ribozymes. Based upon published data, these findings are totally unexpected. Our data are presented below.

Sequences of Mini-ribozymes and Ribozymes

Upper-case letters represent ribonucleotides, and lower-case letters represent deoxyribonucleotides. Substrates are labelled S, followed by the number of nucleotides in the substrate molecule. Minizymes are labelled M, followed by the sequence of the linker connecting the conserved nucleotides $A_9$ and $G_{12}$ (e.g. KrMgtttc is a miniribozyme in the Kruppel system, with a deoxyribonucleotide linker of sequence 5'd(GTTTTC). Full-sized ribozymes which contain a stem-loop II (with 4 b.p. in helix II) are labeled RA (if made of ribonucleotides), RB (with deoxyribonuclotides in the arms which hybridize to the substrates, and ribonucleotides elsewhere), and RC (if made of deoxyribonuclotides, except for the conserved ribonucleotides $C_3$–$A_9$ and $C_{12}$–$C_{15.2}$).

Interleukin-2 system (Seq ID No. 32–38)

IL2S15 (15 mer substrate)
5' UCCUGUCUUGCAUUg 3'

IL2Mgtttc (DNA/RNA mini-ribozyme with d(GTTTC) linker

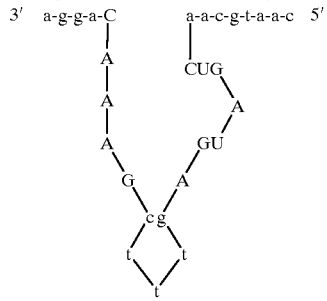

IL2Mgttttc (DNA/RNA mini-ribozyme with d(GTTTTC) linke

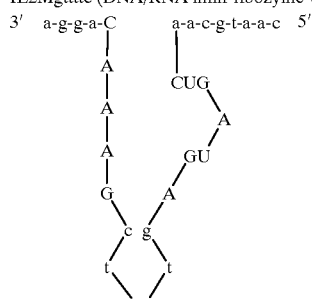

-continued

IL2"RB" DNA-armed ribozyme

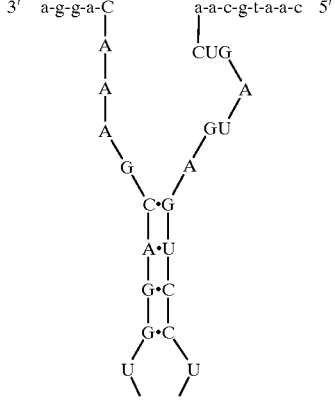

IL2"RC" DNA-containing ribozyme

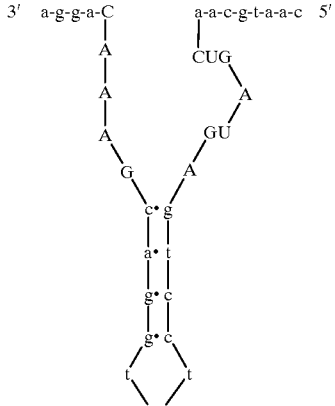

IL2 MGUUUUC(all-RNA miniribozyme with r(GUUUUC) linkers

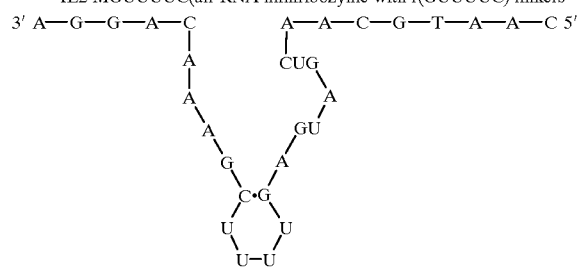

IL2 (all RNA ribozyme)

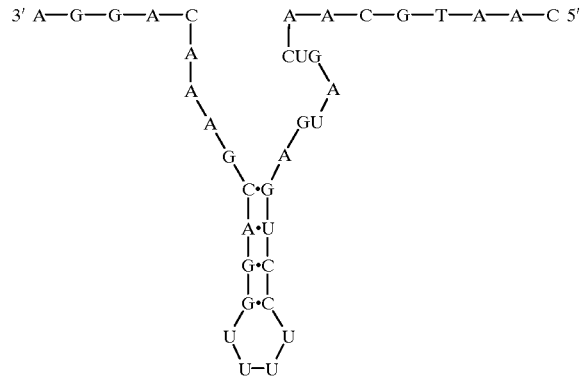

TAT system (Seq ID No. 39–43)
TATS13 (13 mer substrate)
5' GGAAGUCAGCCU a 3'

-continued

TATS21 (21 mer substrate)
5' UCCAGGAAGUCAGCCUAGGA c3'

TATMgtttc (DNA/RNA mini-ribozyme with d(GTTTC) linker
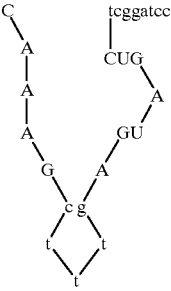

TATMgttttc (DNA/RNA mini-ribozyme with d(GTTTTC) linker
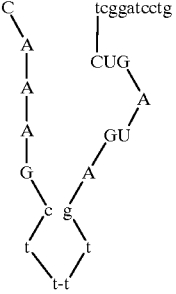

TAT"RC" DNA-containing ribozyme
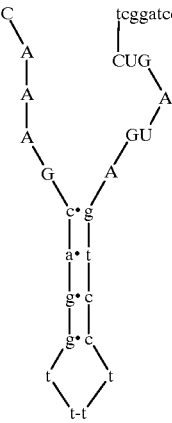

Kr system (Seq ID No. 44–47)
KrS13 (13 mer substrate)
5' GCGAGUCCACAC T 3'

KrS21 (21 mer substrate)
5' AUUUGCGAGUCCACACACUGGA g 3'

KrMgttttc (DNA/RNA mini-ribozyme with d(GTTTTC) linke
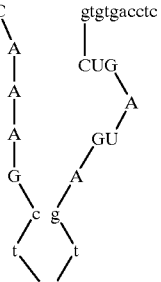

Kr "RC" DNA-containing ribozyme
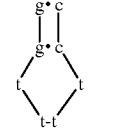

Experimental Data

The method for determining rates of cleavage (kobs) of short substrates by the miniribozymes is as described in Example 1. Initial experiments at pH 8.2 showed the reactions for the TAT and IL2 miniribozymes and "RC" ribozymes are very fast, with the reactions being completed in less than 1 minute. Therefore, the reactions were performed at the lower pH of 7.1 (which in principle should be 12.6-fold slower than the pH 8.2 if the reactions have a first order dependence on OH concentration in this pH range). The data at pH 7.1 show more accurately the relative activities of the various molecules. In the Tables below, values in parentheses($\sigma$) are the standard deviations of at least two independent determinations; and *indicates an initial fast reaction followed by a slower reaction, with for the initial fast reaction being given.

Table 8. $k_{obs}$ (min-1) and %P∞ for KrMgttttc and KrRC cleaving the 13-mer and 21-mer substrates in 10 mM MgCl$_2$, 50 mM Tris.Cl pH 7.1, 37° C., 6 $\mu$M ribozyme/miniribozyme and 4 $\mu$M substrate.

|  | KrMgtttc | | KrRC | |
|---|---|---|---|---|
|  | $k_{obs}$ ($\sigma$) | % P$_{28}\sigma$ | $k_{obs}$ ($\sigma$) | % P$_{28}\sigma$ |
| KrS13 | 0.59* (0.09) | 70(3) | 1.6* (0.3) | 78(2) |
| KrS21 | 3.0* (0.2) | 58(1) | 1.34* (0.08) | 56(1) |

Table 9. $k_{obs}$ (min$^{-1}$) and %P$_\infty$ for TATMgttte, TATMgtttte and TATRC cleaving various substrates in 10 mM MgCl$_2$, 50 mM Tris.Cl pH 7.1, 37° C. Concentration of ribozyme exceeded that of substrate, with concentrations varying between 4 $\mu$M and 8 $\mu$M (ribozyme and miniribozyme) and 2 $\mu$M and 5 $\mu$M (substrate), with typical concentrations being 6 $\mu$M for ribozyme/miniribozyme and 4 $\mu$M for substrate.

|  | TATMgtttc | | | | TATMgttttc | | | | TATRC | | | |
| --- | --- | --- | --- | --- | --- | --- | --- | --- | --- | --- | --- | --- |
|  | $k_{obs}$ | (σ) | % $P_\infty$ | σ | $k_{obs}$ | (σ) | % $P_\infty$ | σ | $k_{obs}$ | (σ) | % $P_\infty$ | σ |
| TATS13 | 0.06 | (0.02) | 78 | (6) | 0.175* | (0.003) | 74 | (7) | 0.43* | (0.008) | 80 | (7) |
| TATS21 | 1.1* | (0.3) | 39 | (1) | 0.9* | (0.2) | 45 | (3) | 0.45* | (0.09) | 31 | (2) |

Table 10. $k_{obs}$ (min$^{-1}$) and %$P_\infty$ for the DNA-containing IL2Mgtttt, IL2Mgttttc, IL2Mgtttc, II2RB and IL2RC, and the all-RNA IL2MGUUUUC and IL2RA cleaving the substrate IL2S15-6/8 in 10 mM MgCl$_2$, 50 mM Tris. Cl pH 7.1, 37° C. Concentration of ribozyme exceeded that of substrate, with concentrations varying between 2.5 μM and 20 μM (ribozyme), and 1 μM and 8 μM (substrate, with typical concentrations being 5 μM for ribozyme/miniribozyme and 2 μM for substrate.

|  | $k_{obs}$ (σ) | % $P_{28}$σ |
| --- | --- | --- |
| IL2Mgtte | 0.119 (0.0004) | 85(4) |
| IL2Mgtttte | 0.19 (0.02) | 82(1) |
| IL2RB | 0.06 (0.02) | 78(5) |
| IL2RC | 0.05 (0.001) | 90(7) |
| IL2MGUUUUC | 0.316 (0.0001) | 76(2) |
| IL2RA | 1.4* (0.2) | 66(1) |

Table 11. Comparing the rates of cleavage of substrates (at 37° C., pH 7.1, 10 mM MgCl$_2$) by the miniribozymes with d(GTTTC) and d(GLTTTTC) linkers relative to that analogous DNA-containing ribozymes RC, and the all-RNA mini-ribozyme with r(GUMUWC) linker relative to the analogous all RNA ribozyme RA.

|  | $k_{obs}$ gtttc/RC | $k_{obs}$ gttttc/RC | $k_{obs}$ GUUUUC/RA |
| --- | --- | --- | --- |
| KrS13 | — | 0.37 | — |
| KrS21 | — | 2.2 | — |
| TATS13 | 0.14 | 0.41 | — |
| TATS21 | 2.4 | 2.0 | — |
| IL2S15 | 2.4 | 3.8 | 0.23 |

Comments

Several of the molecules used (Kr"RC", TAT"RC", IL2S15, IL2Mgttte and IL2"RC") have been synthesized at least twice. The rates of cleavage and extents of cleavage do not vary significantly for molecules from different syntheses.

The IL2 minizyme with d(GTTTT) linker, which has kobs=0.27 min$^{-1}$ at pH 8.2 (and kobs=0.024 (0.005) min$^{-1}$ at pH 7.1), is active in cells (see Example 3). Therefore, the IL2 mini-ribozymes with d(GTTTC) and d(GTTTTC) linkers, which have kobs==0.11 and 0.19 min$^{-1}$, respectively, at pH 7.1, and which target the same site in the IL2 mRNA, are expected to be active in cells. For similar reasons, the all-RNA IL2 mini-ribozyme IL2MGUUUUC, which has kobs=0.316 min at pH 7.1, is expected to be active in cells.

Example D In preliminary experiments, a miniribozyme targeted against interleukin-2 mRNA was shown to have activity against this target in human peripheral blood mononuclear cells. The sequence of the miniribozyme, IL2MGUUUUC, was 5° CAAUGCAA CUGAUGA G7J=C GAAAC AGGa 3' (SEQ. ID NO. 48) where upper-case letters represent RNA and lower-case letters DNA (the 3' nucleotide was DNA for convenience in the chemical synthesis). The experiment to test for activity in cells was performed in the manner described in Example 3 (pages 47–57).

Figure 5:
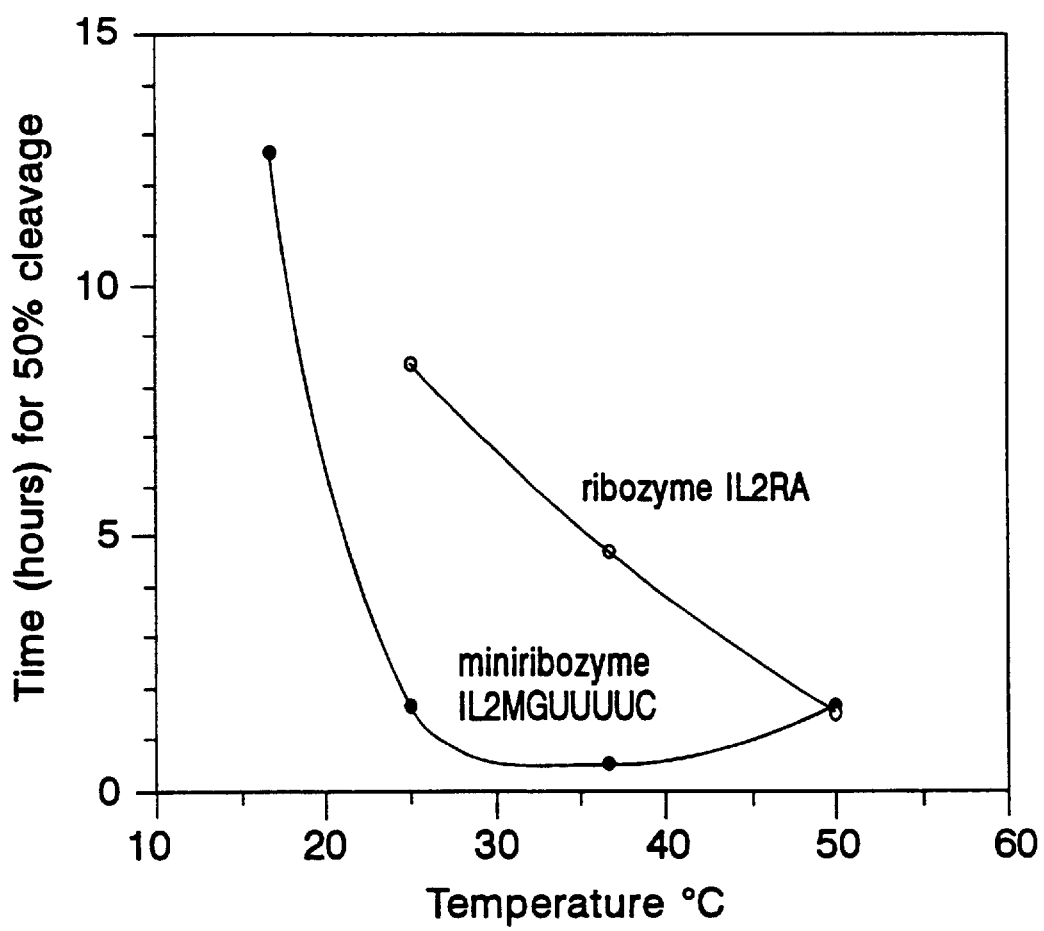
FIG. 5 shows time taken for 500% of an 809-nucleotide interleukin-2 transcript to be cleaved by the miniribozyme IL2MGUUUUC (filled circles) and the ribozyme IL2RA (open circles) as a function of temperature.

Example 6 The interleukin-2 miniribozyme cleaves an 809-nucleotide interleukin-2 transcript much faster in vitro at 37° C. than does an interleukin-2 ribozyme; time taken for 50% of the IL2 transcript to be cleaved is 30 minutes for the miniribozyme and 4.6 hours for the ribozyme. Also, the miniribozyme cleaves the interleukin-2 transcript faster than does the ribozyme over a wide temperature range (please see FIG. 5).

REFERENCES

Altman, S. (1987) *Adv. Enzymol.* 62:1.
Aurup, H., Williams, D. M. & Eckstein, F. (1992), *Biochem.* 31:9636–9641.
Augustyns, K., F. Vandendriessche, A. A. Van, R. Busson, C. Urbanke and P. Herdewijn. (1992), *Nucleic Acids Res.* 20:4711–6.
Baer, M. F., et al. (1990), *Methods Enzymol,* 181:569.
Beaton, G., Dellinger, D., Marshal, W. S. and Caruthers M. H. "Synthesis of oligonucleotide phosphorodithioates" in "Oligonucleotides and Analogues; a Practical Approach" pp 109–136, F. Eckstein (Ed). Oxford University Press, Oxford.
Beijer, B., Grotli, M., Douglas, M. E. and Sproat, B. S. (1994), *Nucleos Nucleon,* 13:1905–1927.
Blommers, M. J., U. Pieles and A. De Mesmaeker (1994), *Nucleic Acids Res.,* 22:4187–4194.
Breaker, R. R. and Joyce, G. F. (1994), *Tibtech,* 12:268–275.
Bruening, G., (1989), *Methods in Enzymology,* 180:546–558.
Bruening, G. (1990), *Seminars in Virol.,* 1:127.
Bryant, J. (1992), *Tibtech,* 10:342–343.
Buzayan et al. (1986), *Proc. Natl. Acad. Sci. USA.* 83:8859–8862.
Buzayan, J. M., van Tol, H., Feldstein, P. A. and Breuning, G. (1990), *Nucleic Acids Res.,* 18: 4447–4451. Phosphate 5' to A9 cannot be phosphorothioate.
Cameron et al. (1989), *Proc. Natl. Acad. Sci. USA,* 86:9139–9143.
Cantor, G. H. et al. (1993), *Proc. Natl. Acad. Sci. USA,* 90:10932–10936.
Cao, X. and M. D. Matteucci (1994), *Tet. Lett.,* 35:2325–2328.
Carruthers et al. (1987), *Methods in Enzymology,* 154: 287–313).
Caruthers, M. H. et al (1991), *Nucleic Acids Symp Ser* (ENGLAND), 24:91–94.
Caulfield, T. J., Prasad, C. V. C., Prouty, C. P., Saha, A. K., Sardaro, M. P., Schairer, W. C., Yawmnan, A., Upson, D. A., Kruse, L. I. (1994), *Bioorg. Med. Chem. Lett.,* 3:2771–2776.
Cech, T. R. (1987), *Science,* 236:1532–1539.
Cech, T. R. et al. (1981), *Cell,* 27:487.

Chen, J. K., R. G. Schultz, D. H. Lloyd and S. M. Gryaznov (1995), *Nucleic Acids Res.*, 23(14):2661–2668.

Chur, A., B. Holst, O. Dahl, H. P. Valentin and E. B. Pedersen (1993), *Nucleic Acids Res.*, 21(22):5179–83.

Conrad, F. et al. (1995), *Nuc Acids Res.*, 23:1845–1853.

Cotten, M. (1990), *Tibtech.* 8:174–178.

Cotten, M. et al. (1989), *The EMBO Journal,* 8:3861–3866.

Debart, F., Rayner, B., Degols, G., & Imbach, J-L. (1992A), *Nucl. Acids. Res.* 20:1193–1200.

Debart, F., J. J. Vasseur, Y. S. Sanghvi and P. D. Cook. (1992B), *Bioorg. Med. Chem. Lett.,* 2:1479–1482.

De Mesmaeker, A., J. Lebreton, A. Waldner, V. Frisch, R. M. Wolf and S. M. Freier (1993), *Synlett,* 733–736.

De Mesmaeker, A., J. Lebreton, A. Waldner, V. Frisch and R. M. Wolf. (1994A), *Bioorg. Med. Chem. Lett.,* 4:873–878.

De Mesmaeker, A., A. Waldner, J. Lebreton, P. Hoffmann, V. Frisch, R. M. Wolf and S. M. Freier. (1994B), *Angew. Chem. Int. Ed.,* 33:226–229.

De Mesmaeker, A., A. Waldner, Y. S. Sangvhi and J. Lebreton. (1994C), *Bioorg. Med. Chem. Lett.,* 4:395–398.

De Mesmaeker, A., A. Waldner, Y. S. Sangvhi and J. Lebreton. (1994), *Bioorg. Med. Chem. Lett.,* 4:395–398.

De Mesmaeker, A., Altmann, K. H., Walcter, A., Wenderborn, S. (1995), *Current Opinion in Structural Biology.* 5:343–355.

Egholm, M., O. Buchardt, L. Christensen, C. Behrens, S. M. Freier, D. A. Driver, R. H. Berg, S. K. Kim, B. Norden and P. E. Nielsen. (1993), *Nature,* 365:566–8.

Egholm, M., O. Buchardt, P. E. Nielsen and R. H. Berg. (1992A), *JACS,* 114:1895–1897.

Egholm, M., P. E. Nielsen, O. Buchardt and R. H. Berg. (1992B), *JACS,* 114:9677–9678.

Eldrup, A. B., K. Bjergarde, J. Felding, J. Kehler and O. Dahl. (1994), *Nucleic Acids Res.,* 2296(1082):1797–1804.

Epstein, L. M., and Gall, J. G., (1987) *Cell* 48:535.

Epstein, L. M., and Gall, J. G., (1989) *Cold Spring Harbour Symp. Quant. Biol.* 52:261.

Evans, G. J., et al. (1992) *Biochem. Soc. Trans.* 20:344S.

Fathi, R., Q. Huang, G. Coppola, W. Delaney, R. Teasdale, A. M. Krieg and A. F. Cook. (1994A), Nucleic Acids Res. 22(24). 5416–5424.

Fathi, R., Q. Huang, J. L. Syi, W. Delaney and A. F. Cook. (1994B), Bioconjug Chem. 5(1). 47–57.

Foehler et al. (Nucleic Acids Research (1986) 14: 5399–407).

Friedman, T., (1989) Science 244: 1275–1280.

Froehler, B., P. Ng and M. Matteucci. (1988), Nucleic Acids Res., 16(11). 4831–9.

Fu, D. J. and L. W. McLaughlin. (1992A), Proc Natl Acad Sci U S A. 89(9). 3985–9.(G5, G8 can't be DNA. A6 and A9 can be DNA. G5 can't be inosine. G8 can be inosine, and A6 and A9 can be purine.)

Fu, D.-J. and McLaughlin, L. W. (1992B), Biochemistry, 31, 10941–10949. Can't change atom N(7) to C(7) in A6; but can change N(7) to C(7) in A9, A13, A14, A15.1.

Fu, D.-J., S. B. Rajur and L. W. McLaughlin. (1993), Biochemistry. 32 10629–10637.

Fu, D.-J. and L. W. McLaughlin. (1992), *Biochemistry.* 31 10941–10949.

Garbesi, A., M. L. Capobianco, F. P. Colonna, L. Tondelli, F. Arcamone, G. Manzini, C. W. Hilbers, J. M. Aelen and M. J. Blommers. (1993), *Nucleic Acids Res.* 21, 4159–65.

Goodchild, J. (1992), Nucleic Acids Res. 20, 4607–4612. 2'-O-methylation in hybridizing arms; enhances cleavage and improves resistance to nucleases.

Grasby, J. A., P. Jonathan, G. Butler and M. J. Gait. (1993), Nucleic Acids Res. 21(19). 4444–50.

Gryaznov, S. M. and R. L. Letsinger. (1992A), Nucleic Acids Res. 20(13). 3403–9.

Gryaznov, S. M. and R. L. Letsinger. (1992B), Nucleic Acids Res. 20(13). 3403–9.

Gryaznov, S. M., D. H. Lloyd, J. K. Chen, R. G. Schultz, L. A. DeDionisio, L. Ratmeyer and W. D. Wilson. (1995), Proc Natl Acad Sci USA. 92(13). 5798–5802.

Green, R., and Szostak, J. W. (1992) *Science* 258:1910.

Habus, I., J. Temsamani and S. Agrawal. (1994), Biorg. Med. Chem. Lett. 4 1065–1070.

Hanahan et al., (1983), J. Mol. Biol 166).

Hanvey, J. C., N. J. Peffer, J. E. Bisi, S. A. Thomson, R. Cadilla, J. A. Josey, D. J. Ricca, C. F. Hassman, M. A. Bonham, K. G. Au and a. l. et. (1992), Science. 258 (5087). 1481–5.

Haseloff, J. and W. L. Gerlach, (1988) Nature, 334:585–591.

Heidenreich, O. and Eckstein, F. (1992), J. Biol. Chem., 267, 1904–1909. 2'-fluorocytidine substitutions have no effect on cleavage rates, but 2'-fluorouridine substitutions cause 5-fold decrease in $k_{cat}/K_M$. One 5' terminal and three 3' terminal phosphorothioate groups have little effect on rates. Putting all pyrimidines as 2'-fluoropyrimidines, and using the one 5' terminal and three 3' terminal chosphorothioate groups, gave a 7-fold reduction in $k_{cat}/K_M$, and 50-fold improvement in stability.

Heidenreich, O., Benseler, F., Fahrenholz, A. and Eckstein, F. (1994), *J Biol Chem* 269, 2131–2138.

Hendry, P. et al (1994), *Biochim et Biophys Acta,* 1219: 405–412.

Herschlag, D., and Cech, T. R. (1990) *Nature* 344:405.

Hogan, B. et al., (1986), Manipulating the Mouse Embryo, A Laboratory Manual, Cold Spring Harbor.

Hogan, B. et al., (1989), Science, 244: 1275.

Homann, M., et al. (1993) *Nucleic Acid Res.* 28:2809–2814.

Idsiak, I., G. Just, M. J. Damha and P. A. Gianaris. (1993), Tet. Lett. 34 5417–5420.

Jager, A., M. J. Levy and S. M. Hecht. (1988), Biochemistry. 27(19). 7237–46.

Jones, R. J., K. Y. Lin, J. F. Milligan, S. Wadwani and M. D. Matteucci. (1993), J. Org. Chem. 58 2983–2991.

Kruger, K., et al. (1982) *Cell* 31:147.

Lamb, J. W. & Hay, R. T., (1990) J. Gen. Virol., 71:2257–2264.

Lebreton, J., A. De Mesmaeker, A. Waldner, V. Fritsch, R. Wolf and S. M. Freier. (1993), Tet. Lett. 34 6383–6386.

Lebreton, J., A. Waldner, C. Lesueur and A. De Mesmaeker. (1994A), Synlett, 137–140.

Lebreton, J., A. Waldner, V. Fritsch, R. M. Wolf and A. De Mesmaeker. (1994B), *Tet. Lett.* 35 5223–5228.

Letsinger, R. L., Singman, C. N., Histand, G., Salunkhe, M. (1988), J. Am. Chem. Soc., 110, 4470–4471.

L'Huillier, P. J. L., et al. (1992) *EMBO* 11:4411–4418.

Llewellyn et al., (1987), J. Mol. Biol., 195: 115–123.

Long, D. M. & Uhlenbeck, O. C., (1994), Proc. National Acd. US 91:6977–6981.

Maliga, P. (1993) Tibtech 11:101–106.

Matteucci, M. D. (1990), Tet. Lett. 31:2385–2388.

Mazzolini, L., et al. (1992) *Plant Molecular Biology* 20:715–731.

McCall, M. J., Hendry, P. and Jennings, P. A. (1992) *Proc. Natl. Acad. Sci. USA,* 89, 5710–5714.

Miller P. S., Bahn, P., Cushman, C D., Kean, J. M., Levis, J. T. (1991), Nucleosides and Nucleotides, 10, 27–46.

Monia, B. P., E. A. Lesnik, C. Gonzalez, W. F. Lima, D. McGee, C. J. Guinosso, A. M. Kawasaki, P. D. Cook and S. M. Freier. (1993), J Biol Chem. 268(19). 14514–22.

Ng, M. M. P., F. Benseler, T. Tuschl and F. Eckstein. (1994), Biochemistry 33(40). 12119–12126.

Nichols, M., et al. (1988) *Proc. Natl. Acad. Sci. U.S.A.* 85:1379.

Nielsen, P. E., M. Egholm, R. H. Berg and O. Buchardt. (1993A), Anticancer Drug Des. 8(1). 53–63.

Nielsen, P. E., M. Egholm, R. H. Berg and O. Buchardt. (1993B), Nucleic Acids Res. 21(2). 197–200.

Noller, H. F., et al. (1992) *Science* 256:1416.

Odai, O., Hiroaki, H., Sakata, T., Tanaka, T. and Uesugi, S. (1990), FEBS Lett. 267, 150–152. G5 cannot be inosine; the 2-amino group seems to be important for stability.

Olsen, D. B., F. Benseler, H. Aurup, W. A. Picken and F. Eckstein. (1991), Biochem. 30 9735–9741.(Single 2'-fluoro or 2'-H (DNA) substitutions on adenosines have little effect on cleavage, but results are additive, so that cleavage drops as more modifications are added. 2'deoxy or 2'-fluoro modifications at A6 and A9 are OK; A13–A15.1 are more sensitive.)

Pace, N. R., and Smith, D., (1990) *J. Biol. Chem.* 265:3587.

Pan, T., and Uhlenbeck, O. C. (1992) *Nature* 358:560.

Paolella, G., Sproat, B. S. and Lamond, A. I. (1992), EMBO J. 11, 1913–1919. Can make all nucleotides 2'-O-allyl ribonucleotides except U4, GS, A6, GS, G12, A15.1. Of these six ribonucleotides, either U4 or A6, but not both, may be 2'-O-allyl, without much loss in activity, but better activity is achieved if U4 and A6 are unmodified RNA. With U4, G5, A6, G8 and A15.1 as RNA and other nucleotides 2'-C-allyl, G12 can be DNA.

Perreault, J.-P., Wu, T., Cousineau, B., Ogilvie, K.K. and Cedergren, R. (1990), Nature, 344, 565–567. Putting DNA into conserved nucleotides A6, G8, A9, G12, A13 and A14 reduces activity, but doesn't eliminate it. Making G5 as DNA results in big reduction in activity.

Perreault, J.-P., Labuda, D., Usman, N., Yang, J.-H. and Cedergren, R. (1991), Biochemistry, 30, 4020–4025. G5 and A9 cannot be DNA. G12, A13, A14, G8 can be DNA.

Perriman, R., et al. (1993) *Antisense Res. & Dev.* 3:253–263.

Piccirilli, J. A., et al. (1992) *Science* 256:1420.

Pieken, W. A., Olsen, D. B., Aurup, H., Williams, D. M., Heidenreich, O., Benseler, F., and Eckstein, F. (1991), Nucleic Acids Res. Symposium Series, 24. (2'amino group at C15.2 (together with 3 other 2'-amino Cs in hybridizing arms) has reduction in activity. Can't have 2'-amino at G5, but can at G12.)

Pieken, W. A., Olsen, D. B., Benseler, F., Aurup, H. and Eckstein, F. (1991), Science, 253, 314–317. Can make all cytidines (C3, C15.2) and uridines (U4, U7) 2'-fluoro or 2'-amino and not get much reduction in cleavage activity. A9 can be 2'-fluoro, but A13, A14 and AIS together cannot have 2'-fluoro group.

Pyle, A. M. (1993) *Science* 261:709–714.

Robertson, D. L., and Joyce, G. F. (1990) *Nature* 344:467.

Ruffner, D. E. and Uhlenbeck, O. C. (1990) "Thiophosphate interference exeriments locate phosphates important for the hammerhead RNA self-cleavage reaction" Nucleic Acids Res., 18: 6025–6029.

Sambrook, J. et al., (1989), Molecular Cloning, A Laboratory Manual, 2nd Edition, Cold Spring Harbor Press.

Saenger, W. (1984), Principles of Nucleic Acid Structure, Springer-Verlag, N.Y.

Sanghvi, Y. S., G. D. Hoke, S. M. Frier, M. C. Zounes, C. Gonzalez, L. Cummins, H. Sasmor and P. D. Cook. (1993). Antisense oligodeoxymucleotides: synthesis, biophysical and biological evaluation of ODN containing modified pyrimidines. NAR. 21 3197–3202.

Saville, B. J. and Collins, R. A. (1990) *Cell* 61:685.

Saxena, S. et al., (1990) J. Biol. Chem., 265:17106–17109.

Seela, F., K. Mersmann, J. A. Grasby and M. J. Gait. (1993). 7-deazaadenosine-oligoribonucleotide building block synthesis and autocatalytic hydrolysis of base modified hammerhead ribozymes. Helv. Chim. Acta. 76 1809–1820.

Shaw, J.-P., Kent, K., Bird, J., Fishback, J. and Froehler, B. (1991) Nucleic Acids Res., 19, 747–750. Degradation of oligodeoxynucleotides in fetal calf serum and cell supernatant is predominantly by 3'exonucleases. Good protection from these 3'exonucleases (and little change in melting temperatures of duplexes) is achieved by synthesizing oligodeoxyribonucleotides with one or two methoxyethyleneamine(MEA) phosphoroarnidate substitutions at the 3' end, or by an inverted linkage (3'-3') using an inverted diester or an inverted phosphoroamidate. Uniformly substituted phosphorothioate oligonucleotides were also very stable to 3'exonucleases, but melting temperatures of duplexes were lowered by 10° C.

Shimamoto, K., Terada, R., Izawa, T., and Fujimoto, H. (1989) Nature 338:274–276.

Shimayama, T., Nishikawa, F., Nishikawa, S. and Taira, K. (1993) Nuclease-resistant chimeric ribozymes containing deoxyribonucleotides and phosphorothioate linkages. Nucleic Acids Res. 21, 2605–2611. Most stable and active Rz had phosphorothioate-DNA in stems I, II and III, as well as thio on 3, side of rC3, rU4, rA9, rC15.2; rN7 is rA or rG (not thio). Protocol given for synthesis and workup of chimeric thio-DNA/RNA ribozymes.

Sinha, N. D., Biernat, J, & Koster, H. (1984) *Nucl. Acids. Res.*12, 4539–4557.

Sioud, M. and Drlica, K. (1991) *Proc. Natl. Acad. Sci. U.S.A.* 88:7303–7307.

Sioud, M. (1994) *J. Mol. Biol.,* 242, 619-629. Slim, G. and M. Gait. (1992). The role of the exocyclic amino groups of conserved purines in hammerhead ribozyme cleavage. Biochem. Biophys. Res. Commun. 183 605–609.(G12 cannot be inosine; A13, A15.1 cannot be purine. A14 can be purine. G8 can be inosine (but rates down 10-fold) and A9 can be purine (but rates down 6-fold).)

Sleigh, M. J. *Anal. Biochem.* 156, 251–256 (1986)

Strobel, S. A. et al., (1991), Nature 350: 172–174 and references therein.

Sober, H. (1970), CRC Handbook of Biochemistry, Second edition.

Sproat et al. (Oligonucleotide Synthesis—A Practical Approach, IRL Press, Oxford (1984) M. J. Gait—Editor, pp. 83–115).

Sproat, B. S. and Lamond, A. I. (1991A) 2'-O-methyloligoribonucleotides: Synthesis and applications. in "Oligonucleotides and Analogues; a Practical Appraoch" pp 49–86, F. Eckstein (Ed). Oxford University Press, Oxford.

Sproat, B. S., A. I. Lamond, R. G. Garcia, B. Beijer, U. Pieles, M. Douglas, K. Bohmann, F. M. Carmo, S. Weston and S. O'Loughlin. (1991B). 2'-O-alkyloligoribonucleotides, synthesis and applications in molecular biology. Nucleic Acids Symp Ser. 1991 (24). 59-62.

Stec W J; Grajkowski A; Koziolkiewicz M; Uznanski B (1992) Novel route to oligo(deoxyribonucleoside phosphorothioates). Stereocontrolled synthesis of P-chiral oligo(deoxyribonucleoside phosphorothioates. Nucleic Acids Res. 19, 5883–8.

Stirchak, E. P., J. E. Summerton and D. D. Weller. (1987). Uncharged stereoregular nucleic acid analogues.1. Synthesis of a cytosine containing oligomer with carbamate internucleoside linkages. *J. Org. Chem.* 52 4202–4206.

Sullenger, B. A. and Cech, T. R. (1993) *Science* 262:1566–1569.

Summers, M. F., C. Powell, W. Egan, R. A. Byrd, W. D. Wilson and G. Zon. (1986). Alkyl phosphotriester modified oligodeoxyribonucleotides. VI. NMR and UV spectroscopic studies of ethyl phosphotriester (Et) modified Rp—Rp and Sp—Sp duplexes, (d[GGAA(Et)TTCC])2. Nucleic Acids Res. 14(18). 7421–36.

Symons, R. H., (1989) TIBS, 14:445–450.

Symons, R. H., (1990) *Seminars in Virol.* 1:117.

Szabo, T., A. Kers and J. Stawinski. (1995). A new approach to the synthesis of the 5'-deoxy-5'-mesthylphosphonate linked thymidine oligonucleotide analogues. Nucleic Acids Res. 2380(60204). 893–900.

Szostak, J. W. (1992) TIBS 17:89–93.

Taylor, J., (1990) *Seminars in Virol.* 1:135.

Tuschl, T. & Eckstein, F., (1993), PNAS, 90:6991–6994.

Uhlmann et al., (1990), Chem. Revs., 90:544–584.

Tuschl, T., M. M. P. Ng, W. Piekeri, F. Benseler and F. Eckstein. (1993). Importance of exocyclic base functional groups of central core guanosines for hammerhead ribozyme activity. Biochemistry. 32(43). 11658–11668.

Usman, N., Beigelman, L., Draper, K., Wincott, F and McSwiggen, J. (1995) RNA synthesis and ribozymes. J. Cellular Biochemistry, Absract supplement 19A, Abstract A6-018, p 205. Details given in talk at 24th Keystone symposium on *Ribozymes: basic science and therapeutic applications*.

Vasseur, J. J., F. Debart, Y. S. Sanghvi and P. D. Cook. (1992). Oligonucleosides: synthesis of a novel methylhydroxylamidelinked nucleoside dimer into antisense oligonucleotides. J.Am. Chem. Soc. 114 4006–4007.

Vyazovkina, E. V., E. V. Savchenko, S. G. Lokhov, J. W. Engels, E. Wickstrom and A. V. Lebedev. (1994). Synthesis of specific diastereomers of a DNA methylphosphonate heptamer, d(CpCpApApApCpA), and stability of base pairing with the normal DNA octamer d(TPGPTPTPTPGPGPC). Nucleic Acids Res. 2202 (1287). 2404–2409.

Waldner, A., A. De Mesmaeker and J. Lebreton. (1994A). Synthesis of oligodeoxyriboneucleotides containing dimers with carbamate moieties as replacement of the the natural phosphodiester linkage. *Bioorg. Med. Chem. Lett.* 4 405–408.

Waldner, A. and A. De Mesmaeker. (1995). Thiocarbamates as novel backbone replacements in oligonucleotides. Synlett. 108–110.

Waldner, A., A. De Mesmaeker, J. Lebreton, V. Fritsch and R. M. Wolf. (1994B). Ureas as backbone replacements for the phosphodiester linkage in oligonucleotides. Synlett. 57–61.

Waugh, D.S., et al. (1989) *Science* 244:1569.

Williams, D. M., Pieken, W. A. and Eckstein, F. (1992) Function of specific 2'-hydroxyl groups of guanosines in a hammerhead ribozyme probed by 2' modifications. Proc. Natl. Acad. Sci. USA, 89, 918–921. G5 and G8 cannot have 2'F, 2'H, or 2'amino (reduction in k(cat) is about 150-fold for 2'F, 2'H, and about 10-fold for 2'amino). G12 can have 2'H and 2'amino, but cannot have 2'F. Yang, et al., (1990) Biochemistry 29:11156–11160.

Yang, J.-H., Usman, N., Chartrand, P. and Cedergren, R. (1992) Minimum ribonucleotide requirement for catalysis by the RNA hammerhead domain. Biochemistry, 31, 5005–5009. DNA is OK at C3, T4, A6, T7, G12, A13, A14. Can't have DNA at G5, A15.1. If lots of sites are DNA, then rates drop dramatically if G8 is DNA or G15.2 is DNA.

Zaug, A. J. et al, (1984), Science, 224:574–578.

Zaug, A. J. & Cech, T. R., (1986a) Science, 231:473–474.

Zaug, A. J. et al., (1986b) Nature, 324:429–433.

Zaug, A. J., and Cech, T. R. (1986) *Biochemistry* 25:4478.

Zhao, J. J. and Pick, L. (1993) *Nature* 365:448–451.

What is claimed is:

1. A compound having the formula:

$$3'\ (X)_n\ \text{...}\ (X)_{n'}\ 5'$$

(structure with A-A-G-T/U-(T/U)$_b$-G-A-A-G-X, containing $(X)_a$ bridge, C-U-G on right side)

3' $(X)_n$-(Seq. ID No. 51)-(T/U)$_b$—G—(X)$_{n'}$-(Seq. ID No. 52)-(X)$_{n'}$ 5' wherein each X represents a nucleotide which may be the same or different and may be modified in its sugar, base or phosphate;

wherein each of A, C, G, U, and T represents a nucleotide which may be substituted or modified in its sugar, base or phosphate;

wherein (T/U)—(T/U)$_b$—G represents T—(T)$_b$—G or U—(U)$_b$—G, with the proviso that b represents an integer which is 3, 4 or 5;

wherein each of $(X)_n$ and $(X)_{n'}$ represents an oligonucleotide having a predetermined sequence which is capable of hybridizing with an RNA target sequence;

wherein each of n and n' represents an integer which defines the number of nucleotides in the oligonucleotide;

wherein each solid line represents a covalent bond between the nucleotides located on either side thereof; and wherein a represents an integer which defines a number of nucleotides with the proviso that a may be 0 or 1 and if 0, the A located 5' of $(X)_a$ is bonded to the G located 3' of $(X)_a$.

2. The compound of claim 1, wherein the oligonucleotide 3'-$(X)_n$— is 3'-$(X)_{n-1}$—A—.

3. The compound of claim 1, wherein the oligonucleotide 3'-$(X)_n$— is 3'-$(X)_{n-2}$—C—A—.

4. A compound having the formula:

$$3'\ (X)_{n-1}\text{—}A\ \text{...}\ (X)_{n'}\ 5'$$

(structure with A-A-G-(T/U)-Q-(T/U)$_b$-G-A-A-G-X, containing $(X)_a$ bridge, C-U-G on right side)

3' $(X)_n$-(Seq. ID No. 53)-(T/U)$_b$—G—(X)$_a$-(Seq. ID NO. 52)-(X)$_{n'}$ 5' wherein each X represents a nucleotide which may be the same or different and Q represents guanylate or deoxyguanylate and both of which may be modified in their sugar, base or phosphate;

wherein each of A, C, G, U, and T represents a nucleotide which may be substituted or modified in its sugar, base or phosphate;

wherein (T/U)—(T/U)$_b$—Q represents T—(T)$_b$—Q or U—(U)$_b$—Q, with the proviso that b represents an integer which is 3, 4 or 5;

wherein each of (X)$_{n-1}$—A and (X)$_{n'}$ represents an oligonucleotide having a predetermined sequence which is capable of hybridizing with an RNA target sequence;

wherein each of n and n' represents an integer which defines the number of nucleotides in the oligonucleotide such that (X)$_{n-1}$—A and (X)$_{n'}$ are sufficient to hybridize to the target sequence;

wherein each solid line represents a covalent bond between the nucleotides located on either side thereof; and wherein a represents an integer which defines a number of nucleotides with the proviso that a may be 0 or 1 and if 0, the A located 5' of (X)$_a$ is bonded to the Q located 3' of (X)$_a$.

5. The compound of claim 4, wherein the oligonucleotide 3'-(X)$_{n-1}$—A is 3'-(X)$_{n-2}$—C—A—.

6. The compound of claim 4, wherein each X and Q is a deoxyribonucleotide.

7. The compound of claim 4, wherein each X and Q is a ribonucleotide.

8. The compound of claim 1 or 4, wherein (X)$_a$ is absent.

9. The compound of claim 1 or 4, wherein the integer b of (T/U)$_b$ is equal to 3.

10. The compound of claim 1 or 4, wherein the integer b of (T/U)$_b$ is equal to 4.

11. The compound of claim 1, wherein each X is a deoxyribonucleotide.

12. The compound of claim 1, wherein each X is a ribonucleotide.

13. The compound of claim 1 or 4, wherein (T/U)$_b$ is a (T)$_b$.

14. The compound of claim 1 or 4, wherein (T/U)$_b$ is (U)$_b$.

15. A compound having the formula:

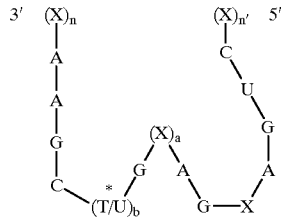

3' (X)$_n$-(Seq. ID NO. 54)-(T/U)$_b$—G—(X)$_a$-(Seq. ID NO. 52)-(X)$_{n'}$ 5' wherein each X represents a nucleotide which may be the same or different and may be substituted or modified in its sugar, base or phosphate;

wherein each of A, C, G, U, and T represents a nucleotide which may be modified in its sugar, base or phosphate;

wherein C—(T/U)$_b$—G represents C—(T)$_b$—G or C—(U)$_b$—G, with the proviso that b represents an integer which is 3, 4 or 5;

wherein each of (X)$_n$ and (X)$_{n'}$ represents an oligonucleotide having a predetermined sequence which is capable of hybridizing with an RNA target sequence;

wherein each of n and n' represents an integer which defines the number of nucleotides in the oligonucleotide;

wherein * represents a base pair between the nucleotides located on either side thereof;

wherein each solid line represents a covalent bond between the nucleotides located on either side thereof; and wherein a represents an integer which defines a number of nucleotides with the proviso that a may be 0 or 1 and if 0, the A located 5' of (X)$_a$ is bonded to the G located 3' of (X)$_a$.

16. A compound having the formula:

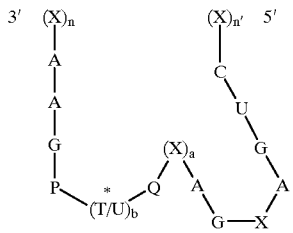

3' (X)$_n$-(Seg. ID NO. 55)-P—(T/U)$_b$—Q—(X)$_a$-(Seg. ID NO. 52)-(X)$_{n'}$ 5' wherein each X represents a nucleotide which may be the same or different, P represents cytidylate or deoxycytidylate, Q represents guanvlate or deoxyguanylate and each or which may be substituted or modified in their sugar, base or phosphate;

wherein each of A, C, G, U, and T represents a nucleotide which may be modified in its sugar, base or phosphate;

wherein P—(T/U)$_b$—Q represents P—(T)$_b$—Q or P—(U)$_b$—Q, with the proviso that b represents an integer which is 3, 4 or 5;

wherein each of (X)$_n$ and (X)$_{n'}$ represents an oligonucleotide having a predetermined sequence which is capable of hybridizing with an RNA target sequence;

wherein each of n and n' represents an integer which defines the number of nucleotides in the oligonucleotide such that (X)$_n$ and (X)$_{n'}$ are sufficient to hybridize to the target sequence;

wherein * represents a base pair between the nucleotides located on either side thereof;

wherein each solid line represents a covalent bond between the nucleotides located on either side thereof; and wherein a represents an integer which defines a number of nucleotides with the proviso that a may be 0 or 1 and if 0, the A located 5' of (X)$_a$ is bonded to the Q located 3' of (X)$_a$.

17. The compound of claim 15 or 16, wherein the oligonucleotide 3'-(X)$_n$— is 3'-(X)$_{n-1}$—A—.

18. The compound of claim 15 or 16, wherein the oligonucleotide 3'-(X)$_n$— is 3'-(X)$_{n-2}$—C—A—.

19. The compound of claim 15 or 16, wherein (X)$_a$ is absent.

20. The compound of claim 15 or 16, wherein the integer b of (T/U)$_b$ is equal to 3.

21. The compound of claim 15 or 16, wherein the integer b of (T/U)$_b$ is equal to 4.

22. The compound of claim 15, wherein each X is a deoxyribonucleotide.

23. The compound of claim 16, wherein each X, P and Q is a deoxyribonucleotide.

24. The compound of claim 16, wherein each X, P and Q is a ribonucleotide.

25. The compound of claim 15; wherein b is equal to 3 or 4, each x ia a ribonucleotide, and C—(U)$_b$—G is RNA.

26. The compound of claim 15 or 16, wherein (T/U)$_b$ is a (T)$_b$.

27. The compound of claim 15 or 16, wherein (T/U)$_b$ is a (U)$_b$.

28. A composition which comprises a compound of claim 1, 4, 15, or 16 in association with an acceptable carrier.

29. An oligonucleotide transfer vector containing a nucleotide sequence which on transcription gives rise to the compound of claim 1, 4, 15 or 16.

30. The transfer vector of claim 29, wherein the transfer vector is a bacterial plasmid, a bacteriophage DNA, a cosmid, or an eukaryotic viral DNA.

31. The oligonucleotide transfer vector of claim 29, wherein the oligonucleotide transfer vector is a plant DNA virus, a geminivirus or an infective phage particle.

32. The oligonucleotide transfer vector of claim 29, wherein the oligonucleotide transfer vector is packaged and contains the promoter sequences for RNA polymerase II or RNA polymerase III.

33. A host cell transformed by the transfer vector of claim 29.

34. The host cell of claim 33, wherein the host cell is a prokaryotic host cell or an eukaryotic host cell.

35. The prokaryotic host cell of claim 34, wherein the prokaryotic host cell is an *E. coli* host cell.

36. The eukaryotic host cell of claim 34, wherein the eukaryotic host cell is a monkey COS host cell, a Chinese hamster ovary host cell, a mammalian host cell or a plant host cell.

37. The compound of claim 1, 4, 15 or 16 which further comprises an antisense nucleic acid which is capable of hybridizing with an RNA target sequence.

38. The compound of claim 1, 4, 15 or 16 which further comprises at least one additional non-naturally occurring oligonucleotide compound which comprises nucleotides whose sequence defines a conserved catalytic region and nucleotides whose sequence is capable of hybridizing with a predetermined target sequence.

39. The compound of claim 38 wherein the additional non-naturally occurring oligonucleotide compound is a hammerhead ribozyme, a minizyme, a hairpin ribozyme, a hepatitis delta ribozyme, an RNAase P ribozyme or a combination thereof.

40. The compound according to claim 15, comprising the formula:

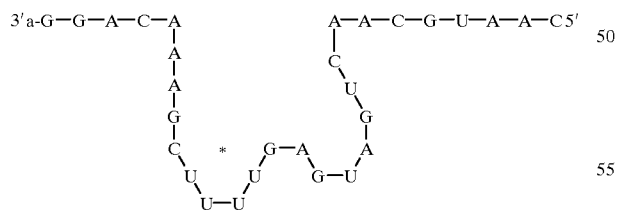

(Seq. ID NO. 37)

wherein each of A, C, G, and U represents a ribonucleotide which may be modified in its sugar, base or phosphate; and wherein a represents a deoxyribonucleotide which may be modified in its sugar, base or phosphate.

41. The compound according to claim 15, comprising the formula:

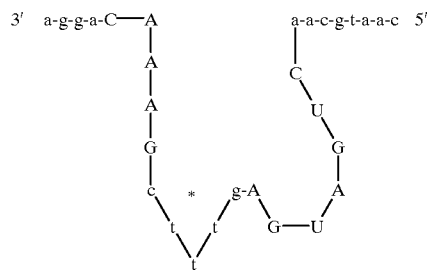

(Seq. ID NO. 33)

wherein each of A, C, G, and U represents a ribonucleotide which may be modified in its sugar, base or phosphate; and wherein each of a, c, g, and t represents a deoxyribonucleotide which may be modified in its sugar, base or phosphate.

42. The compound according to claim 15, comprising the formula:

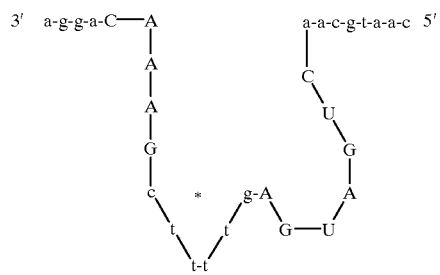

(Seq. ID NO. 34)

wherein each of A, C, G, and U represents a ribonucleotide which may be modified in its sugar, base or phosphate; and wherein each of a, c, g, and t represents a deoxyribonucleotide which may be modified in its sugar, base or phosphate.

43. The compound according to claim 15, comprising the formula:

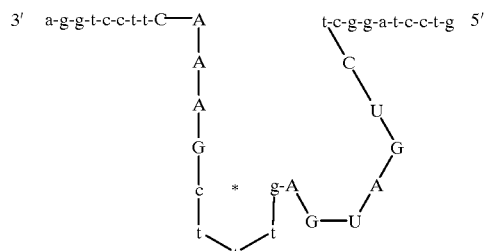

(Seq. ID NO. 41)

wherein each of A, C, G, and U represents a ribonucleotide which may be modified in its sugar, base or phosphate; and wherein each of a, c, g, and t represents a deoxyribonucleotide which may be modified in its sugar, base or phosphate.

44. The compound according to claim 15, comprising the formula:

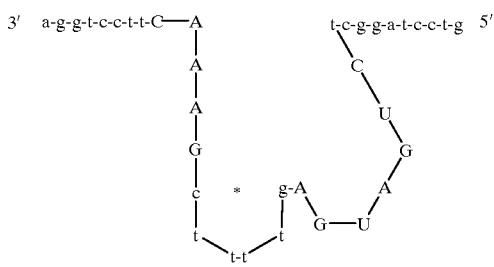

(Seq. ID NO. 42)

wherein each of A, C, G, and U represents a ribonucleotide which may be modified in its sugar, base or phosphate; and wherein each of a, c, g, and t represents a deoxyribonucleotide which may be modified in its sugar, base or phosphate.

45. The compound according to claim 15, comprising the formula:

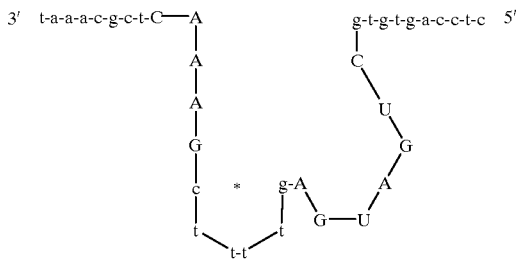

(Seq. ID NO. 46)

wherein each of A, C, G, and U represents a ribonucleotide which may be modified in its sugar, base or phosphate; and wherein each of a, c, g, and t represents a deoxyribonucleotide which may be modified in its sugar, base or phosphate.

46. The compound according to claim 1, comprising the formula:

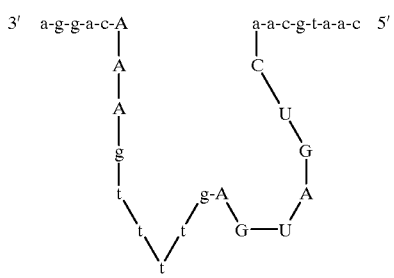

(Seq. ID NO. 27)

wherein each of A, C, G, and U represents a ribonucleotide which may be modified in its sugar, base or phosphate; and wherein each of a, c, g, and t represents a deoxyribonucleotide which may be modified in its sugar, base or phosphate.

---

SEQUENCE LISTING

```
<160> NUMBER OF SEQ ID NOS: 55

<210> SEQ ID NO 1
<211> LENGTH: 13
<212> TYPE: RNA
<213> ORGANISM: Artificial Sequence
<220> FEATURE:
<223> OTHER INFORMATION: Description of Artificial Sequence: Ribozymes
      and portions thereof

<400> SEQUENCE: 1
gcgggucaug aag                                                          13

<210> SEQ ID NO 2
<211> LENGTH: 42
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 2
gacacuucau cugaugaguc cuuuuggacg aaacccgcag gt                          42

<210> SEQ ID NO 3
<211> LENGTH: 17
```

```
<212> TYPE: RNA
<213> ORGANISM: Artificial Sequence
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (1)
<220> FEATURE:
<221> NAME/KEY: misc_RNA
<222> LOCATION: (6)
<220> FEATURE:
<221> NAME/KEY: misc_RNA
<222> LOCATION: (9)
<220> FEATURE:
<221> NAME/KEY: misc_RNA
<222> LOCATION: (17)

<400> SEQUENCE: 3
ncugangang uugaaan                                                        17

<210> SEQ ID NO 4
<211> LENGTH: 17
<212> TYPE: RNA
<213> ORGANISM: Artificial Sequence
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (1)
<220> FEATURE:
<221> NAME/KEY: misc_RNA
<222> LOCATION: (6)
<220> FEATURE:
<221> NAME/KEY: misc_RNA
<222> LOCATION: (9)
<220> FEATURE:
<221> NAME/KEY: misc_RNA
<222> LOCATION: (17)

<400> SEQUENCE: 4
ncugangang ucgaaan                                                        17

<210> SEQ ID NO 5
<211> LENGTH: 29
<212> TYPE: DNA
<213> ORGANISM: Artificial Sequence
<220> FEATURE:
<223> OTHER INFORMATION: Synthetic Ribozyme or  portion thereof
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (1)..(7)
<220> FEATURE:
<221> NAME/KEY: misc_RNA
<222> LOCATION: (25)..(29)

<400> SEQUENCE: 5
nnnnnnncug augagttttg aaacnnnnn                                           29

<210> SEQ ID NO 6
<211> LENGTH: 15
<212> TYPE: RNA
<213> ORGANISM: Artificial Sequence
<220> FEATURE:
<223> OTHER INFORMATION: Description of Artificial Sequence: Ribozymes
      and portions thereof

<400> SEQUENCE: 6
```
uccugucuug cauug                                          15

<210> SEQ ID NO 7
<211> LENGTH: 29
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 7
caatgcaacu gaugagtttt gaaagagga                           29

<210> SEQ ID NO 8
<211> LENGTH: 29
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 8
caatgcaacu gaugagtttt gaaacagga                           29

<210> SEQ ID NO 9
<211> LENGTH: 28
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 9
caatgcaacu gacgaccttg aaacagga                            28

<210> SEQ ID NO 10
<211> LENGTH: 25
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (16)

<400> SEQUENCE: 10
caatgcaacu gaugangaaa cagga                               25

<210> SEQ ID NO 11
<211> LENGTH: 13
<212> TYPE: RNA
<213> ORGANISM: Artificial Sequence
<220> FEATURE:
<223> OTHER INFORMATION: Description of Artificial Sequence: Ribozymes
      and portions thereof

<400> SEQUENCE: 11
ggaagucagc cua                                            13

```
<210> SEQ ID NO 12
<211> LENGTH: 35
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 12
gtcctaggct cugaugagtt ttgaaacttc ctgga                              35

<210> SEQ ID NO 13
<211> LENGTH: 34
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 13
gtcctaggct cugaugattt tgaaacttcc tgga                               34

<210> SEQ ID NO 14
<211> LENGTH: 17
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 14
uuccaugucg gcagaat                                                  17

<210> SEQ ID NO 15
<211> LENGTH: 31
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 15
attctgcccu gaugagtttt gaaacatgga a                                  31

<210> SEQ ID NO 16
<211> LENGTH: 30
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 16
attctgcccu gaugattttg aaacatggaa                                    30

<210> SEQ ID NO 17
<211> LENGTH: 31
<212> TYPE: DNA
<213> ORGANISM: Artificial Sequence
```

```
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 17
attctgcccu gaugaggttt gaaacatgga a                                        31

<210> SEQ ID NO 18
<211> LENGTH: 20
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 18
ccaggcaguc agaucaucut                                                     20

<210> SEQ ID NO 19
<211> LENGTH: 34
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 19
aagatgatct cugaugagtt ttgaaactgc ctgg                                     34

<210> SEQ ID NO 20
<211> LENGTH: 33
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 20
aagatgatct cugaugattt tgaaactgcc tgg                                      33

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (1)..(17)

<400> SEQUENCE: 21
nnnnnnnnnn nnnnnnn                                                        17

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Ribozymes
      and portions thereof
```

```
<400> SEQUENCE: 22
attctgccga catggaa                                               17

<210> SEQ ID NO 23
<211> LENGTH: 31
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 23
attctgcccu gaugagtttt gaaacatgga a                               31

<210> SEQ ID NO 24
<211> LENGTH: 31
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 24
attctgcccu gaugagtttt gagacatgga a                               31

<210> SEQ ID NO 25
<211> LENGTH: 15
<212> TYPE: RNA
<213> ORGANISM: Artificial Sequence
<220> FEATURE:
<223> OTHER INFORMATION: Description of Artificial Sequence: Ribozymes
      and portions thereof

<400> SEQUENCE: 25
uccugucuug cauug                                                 15

<210> SEQ ID NO 26
<211> LENGTH: 36
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 26
caatgcaacu gaugaguccu uuuggacgaa acagga                          36

<210> SEQ ID NO 27
<211> LENGTH: 29
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 27
caatgcaacu gaugagtttt gaaacagga                                  29
```

```
<210> SEQ ID NO 28
<211> LENGTH: 29
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 28
caatgcaacu gaugagtttt gagacagga                                         29

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Ribozymes
      and portions thereof

<400> SEQUENCE: 29
caatgcaaga cagga                                                        15

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Ribozymes
      and portions thereof

<400> SEQUENCE: 30
acgaaagacg ctaag                                                        15

<210> SEQ ID NO 31
<211> LENGTH: 28
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 31
caatgcaacu gacgaccttg aaacagga                                          28

<210> SEQ ID NO 32
<211> LENGTH: 15
<212> TYPE: RNA
<213> ORGANISM: Artificial Sequence
<220> FEATURE:
<223> OTHER INFORMATION: Description of Artificial Sequence: Ribozymes
      and portions thereof

<400> SEQUENCE: 32
uccugucuug cauug                                                        15

<210> SEQ ID NO 33
<211> LENGTH: 29
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof
```

```
<400> SEQUENCE: 33
caatgcaacu gaugagtttc gaaacagga                                29

<210> SEQ ID NO 34
<211> LENGTH: 30
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 34
caatgcaacu gaugagtttt cgaaacagga                               30

<210> SEQ ID NO 35
<211> LENGTH: 36
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 35
caatgcaacu gaugaguccu uuuggacgaa acagga                        36

<210> SEQ ID NO 36
<211> LENGTH: 36
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 36
caatgcaacu gaugagtcct tttggacgaa acagga                        36

<210> SEQ ID NO 37
<211> LENGTH: 30
<212> TYPE: RNA
<213> ORGANISM: Artificial Sequence
<220> FEATURE:
<223> OTHER INFORMATION: Description of Artificial Sequence: Ribozymes
      and portions thereof

<400> SEQUENCE: 37
caaugcaacu gaugaguuuu cgaaacagga                               30

<210> SEQ ID NO 38
<211> LENGTH: 36
<212> TYPE: RNA
<213> ORGANISM: Artificial Sequence
<220> FEATURE:
<223> OTHER INFORMATION: Description of Artificial Sequence: Ribozymes
      and portions thereof

<400> SEQUENCE: 38
caaugcaacu gaugaguccu uuuggacgaa acagga                        36

<210> SEQ ID NO 39
<211> LENGTH: 13
<212> TYPE: RNA
```

```
<213> ORGANISM: Artificial Sequence
<220> FEATURE:
<223> OTHER INFORMATION: Description of Artificial Sequence: Ribozymes
      and portions thereof

<400> SEQUENCE: 39
ggaagucagc cua                                                          13

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Ribozymes
      and portions thereof

<400> SEQUENCE: 40
uccaggaagu cagccuagga                                                   20

<210> SEQ ID NO 41
<211> LENGTH: 35
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 41
gtcctaggct cugaugagtt tcgaaacttc ctgga                                  35

<210> SEQ ID NO 42
<211> LENGTH: 36
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 42
gtcctaggct cugaugagtt ttcgaaactt cctgga                                 36

<210> SEQ ID NO 43
<211> LENGTH: 42
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 43
gtcctaggct cugaugagtc cttttggacg aaacttcctg ga                          42

<210> SEQ ID NO 44
<211> LENGTH: 13
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 44
```

```
gcgaguccac act                                                    13

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Ribozymes
      and portions thereof

<400> SEQUENCE: 45
auuugcgagu ccacacugga g                                           21

<210> SEQ ID NO 46
<211> LENGTH: 36
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 46
ctccagtgtg cugaugagtt ttcgaaactc gcaaat                           36

<210> SEQ ID NO 47
<211> LENGTH: 42
<212> TYPE: DNA
<213> ORGANISM: Artificial Sequence
<220> FEATURE:
<223> OTHER INFORMATION: Synthetic Ribozyme or portion thereof
<220> FEATURE:
<223> OTHER INFORMATION: Description of Artificial Sequence: Ribozymes
      and portions thereof

<400> SEQUENCE: 47
ctccagtgtg cugaugagtc cttttggacg aaactcgcaa at                    42

<210> SEQ ID NO 48
<211> LENGTH: 8
<212> TYPE: RNA
<213> ORGANISM: Artificial Sequence
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (1)
<220> FEATURE:
<221> NAME/KEY: misc_RNA
<222> LOCATION: (6)

<400> SEQUENCE: 48 ncucanga                                                           8

<210> SEQ ID NO 49
<211> LENGTH: 5
<212> TYPE: DNA
<213> ORGANISM: Artificial Sequence
<220> FEATURE:
<223> OTHER INFORMATION: Description of Combined DNA/RNA Molecule:
      Synthetic Ribozyme or portion thereof
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (1)
```

```
<220> FEATURE:
<221> NAME/KEY: misc_RNA
<222> LOCATION: (5)

<400> SEQUENCE: 49 ngaan                                                                        5

<210> SEQ ID NO 50
<211> LENGTH: 6
<212> TYPE: DNA
<213> ORGANISM: Artificial Sequence
<220> FEATURE:
<223> OTHER INFORMATION: Description of Combined DNA/RNA Molecule:
      Synthetic Ribozyme or portion thereof
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (1)
<220> FEATURE:
<221> NAME/KEY: misc_RNA
<222> LOCATION: (6)

<400> SEQUENCE: 50 ncgaan                                                                       6

<210> SEQ ID NO 51
<211> LENGTH: 4
<212> TYPE: DNA
<213> ORGANISM: Artificial Sequence
<220> FEATURE:
<223> OTHER INFORMATION: Description of Combined DNA/RNA Molecule:
      Synthetic Ribozyme or portion thereof
<220> FEATURE:
<223> OTHER INFORMATION: n=t/u
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (1)

<400> SEQUENCE: 51 ngaa                                                                         4

<210> SEQ ID NO 52
<211> LENGTH: 7
<212> TYPE: RNA
<213> ORGANISM: Artificial Sequence
<220> FEATURE:
<223> OTHER INFORMATION: Description of Artificial Sequence: Ribozymes
      and portions thereof
<220> FEATURE:
<221> NAME/KEY: misc_RNA
<222> LOCATION: (5)

<400> SEQUENCE: 52 cuganga                                                                      7

<210> SEQ ID NO 53
<211> LENGTH: 5
<212> TYPE: DNA
<213> ORGANISM: Artificial Sequence
<220> FEATURE:
<223> OTHER INFORMATION: Description of Combined DNA/RNA Molecule:
      Synthetic Ribozyme or portion thereof
<220> FEATURE:
<223> OTHER INFORMATION: n=t/u
<220> FEATURE:
<223> OTHER INFORMATION: Description of Artificial Sequence: Ribozymes
```

```
        and portions thereof
<220> FEATURE:
<221> NAME/KEY: misc_RNA
<222> LOCATION: (1)

<400> SEQUENCE: 53 ngaaa                                                                    5

<210> SEQ ID NO 54
<211> LENGTH: 4
<212> TYPE: DNA
<213> ORGANISM: Artificial Sequence
<220> FEATURE:
<223> OTHER INFORMATION: Description of Combined DNA/RNA Molecule:
      Synthetic Ribozyme or portion thereof
<220> FEATURE:
<223> OTHER INFORMATION: Description of Artificial Sequence: Ribozymes
      and portions thereof

<400> SEQUENCE: 54 cgaa                                                                     4

<210> SEQ ID NO 55
<211> LENGTH: 3
<212> TYPE: DNA
<213> ORGANISM: Artificial Sequence
<220> FEATURE:
<223> OTHER INFORMATION: Description of Combined DNA/RNA Molecule:
      Synthetic Ribozyme or portion thereof
<220> FEATURE:
<223> OTHER INFORMATION: Description of Artificial Sequence: Ribozymes
      and portions thereof

<400> SEQUENCE: 55 gaa                                                                      3
```

\* \* \* \* \*